United States Patent [19]
LaVon et al.

[11] Patent Number: 5,397,316
[45] Date of Patent: Mar. 14, 1995

[54] SLITTED ABSORBENT MEMBERS FOR AQUEOUS BODY FLUIDS FORMED OF EXPANDABLE ABSORBENT MATERIALS

[75] Inventors: Gary D. LaVon, Harrison; Gerald A. Young, Cincinnati; Gregory W. Taylor; Donald C. Roe, both of West Chester; William S. Andes, Springfield, all of Ohio

[73] Assignee: The Procter & Gamble Company, Cincinnati, Ohio

[21] Appl. No.: 82,861

[22] Filed: Jun. 25, 1993

[51] Int. Cl.⁶ .................. A61F 13/15; A61F 13/20
[52] U.S. Cl. .................. 604/369; 604/358; 604/368; 604/378; 604/382; 604/385.1
[58] Field of Search ........... 604/358, 368, 369, 359, 604/360, 378, 370, 374, 375, 382, 385.1; 602/46, 47

[56] References Cited

U.S. PATENT DOCUMENTS

| | | |
|---|---|---|
| 2,073,410 | 3/1937 | Thomas . |
| 2,551,663 | 5/1951 | Fox .................. 604/369 |
| 3,240,657 | 3/1966 | Hynek . |
| 3,654,060 | 4/1972 | Goldman . |
| 3,881,491 | 5/1975 | Whyte .............. 604/385.1 |
| 3,890,974 | 6/1975 | Kozak . |
| 4,269,188 | 5/1981 | Nishizawa et al. . |
| 4,389,211 | 6/1983 | Lenaghan . |
| 4,394,930 | 7/1983 | Korpman .......... 604/369 |
| 4,560,372 | 12/1985 | Pieniak . |
| 4,592,751 | 6/1986 | Gegleys ............ 604/368 |
| 4,643,726 | 2/1987 | Gegleys ............ 604/368 |
| 4,676,784 | 6/1987 | Erdman et al. . |
| 4,676,785 | 6/1987 | Battista ............. 604/369 |
| 4,762,521 | 8/1988 | Roessler et al. . |
| 4,773,408 | 9/1988 | Cilento et al. ..... 604/368 |
| 4,787,896 | 11/1988 | Houghton ......... 604/385.1 |
| 5,147,345 | 9/1992 | Young et al. . |
| 5,149,720 | 9/1992 | DesMarais et al. . |
| 5,236,965 | 8/1993 | Engelhardt et al. .......... 604/369 |

FOREIGN PATENT DOCUMENTS

| | | |
|---|---|---|
| 0160569 | 11/1985 | European Pat. Off. . |
| 0293208B | 11/1988 | European Pat. Off. . |

Primary Examiner—Randall L. Green
Assistant Examiner—P. Zuttarelli
Attorney, Agent, or Firm—William Scott Andes; Dean L. Garner; John M. Howell

[57] ABSTRACT

This application relates to the use of slitted regions in absorbent members formed of absorbent materials that remain relatively thin until wetted with such fluids. Suitable materials include presently preferred varieties of polymeric foam materials. Single and multi-layered absorbent members incorporating slitted regions are disclosed, as well as the use of pre-formed cup-shaped slits for enhanced initial fluid acquisition. Such slitted regions in combination with planar expansion properties enable the absorbent members to respond dynamically to various fluid loading conditions to create useful structural features. The slitted regions, in combination with absorbent materials having expansion potential in at least one direction within the plane of the absorbent member, cause the slitted regions to buckle and/or deform out of the plane of the absorbent member, thereby causing the slit surfaces to displace angularly and/or translationally with respect to one another. This more fully exposes the slit surfaces to the incoming fluid for improved acquisition capabilities. The use of pre-formed cup-shaped slits enables the absorbent member to more quickly capture and absorb aqueous body fluids, and is particularly useful for containment and dewatering of moist or runny fecal material and higher viscosity fluids and/or those having a higher concentration of particulate material therein such as blood, menses, or wound fluids.

22 Claims, 13 Drawing Sheets

SLITTED ABSORBENT MEMBERS FOR AQUEOUS BODY FLUIDS FORMED OF EXPANDABLE ABSORBENT MATERIALS

FIELD OF THE INVENTION

This application relates to flexible, microporous, absorbent materials having fluid absorption and retention characteristics that make them particularly suitable for absorbing aqueous body fluids, e.g., urine, blood, menses, wound fluids, etc. This application particularly relates to the use of slitted regions in absorbent members formed of absorbent open-celled polymeric foam materials that have the potential for expansion in at least one direction within the plane of the absorbent member when the absorbent foam material absorbs such aqueous body fluids.

BACKGROUND OF THE INVENTION

The development of highly absorbent articles for use as disposable diapers, adult incontinence pads and briefs, catamenial products such as sanitary napkins, and disposable medical products such as bandages and dressings, is the subject of substantial commercial interest. A highly desired characteristic for such products is thinness. For example, thinner diapers are less bulky to wear, fit better under clothing, and are less noticeable. Thinner articles are also more compact in the package, making the articles easier for the consumer to carry and store. Compactness in packaging also results in reduced distribution costs for the manufacturer and distributor, including less shelf space required in the store per absorbent article.

The ability to provide thinner absorbent articles such as diapers has been contingent on the ability to develop relatively thin absorbent cores or structures that can acquire and store large quantities of discharged body fluids, in particular urine. In this regard, the use of certain particulate absorbent polymers often referred to as "hydrogels," "superabsorbents" or "hydrocolloid" materials has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such particulate absorbent polymers in absorbent articles. Indeed, the development of thinner diapers has been the direct consequence of thinner absorbent cores that take advantage of the ability of these particulate absorbent polymers to absorb large quantities of discharged aqueous body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core absorbent structures comprising a fibrous matrix and particulate absorbent polymers useful in fashioning thin, compact, nonbulky diapers.

These particulate absorbent polymers have the ability to retain large volumes of aqueous body fluids, such as urine. A representative example of such particulate absorbent polymers are lightly crosslinked polyacrylates. Like many of the other absorbent polymers, these lightly crosslinked polyacrylates comprise a multiplicity of anionic (charged) carboxy groups attached to the polymer backbone. It is these charged carboxy groups that enable the polymer to absorb aqueous body fluids as the result of osmotic forces.

Besides osmotic forces, absorbency based on capillary forces is also important in many absorbent articles, including diapers. Capillary forces are notable in various everyday phenomena, as exemplified by a paper towel soaking up spilled liquids. Capillary absorbents can offer superior performance in terms of the rate of fluid acquisition and wicking, i.e. the ability to move aqueous fluid away from the point of initial contact. Indeed, the dual-layer core absorbent structures noted above use the fibrous matrix as the primary capillary transport vehicle to move the initially acquired aqueous body fluid throughout the absorbent core so that it can be absorbed and retained by the particulate absorbent polymer positioned in layers or zones of the core.

Other absorbent materials which provide capillary fluid transport capabilities are open-celled polymeric foams. If made appropriately, open-celled polymeric foams provide features of capillary fluid acquisition, transport and storage required for use in high performance absorbent cores for absorbent articles such as diapers. Absorbent articles containing such foams possess desirable wet integrity, provide suitable fit throughout the entire period the article is worn, and avoid degradation in shape during use. In addition, absorbent articles containing such foam structures are easier to manufacture on a commercial scale. For example, absorbent diaper cores could simply be cut out of continuous foam sheets and could be designed to have considerably greater integrity and uniformity than air-laid fibrous absorbent cores containing particulate absorbent polymers. Such foams could also be molded in any desired shape, or even formed into integral, unitary diapers.

Literature and commercial practice is replete with descriptions of various types of polymeric foams that can imbibe a variety of fluids for a variety of purposes. Indeed, employment of certain types of polymeric foam materials as elements of absorbent articles such as diapers and catamenial products has previously been suggested. See, for example, U.S. Pat. No. 4,029,100 (Karami), issued Jun. 14, 1977, that discloses a shape-retaining diaper that can employ a foam element in the crotch area of its absorbent pad assembly in order to provide high wet resiliency. Certain types of polymeric foam materials have also been suggested as useful in absorbent articles for the purpose of actually imbibing, wicking and/or retaining aqueous body fluids. See, for example, U.S. Pat. No. 3,563,243 (Lindquist), issued Feb. 6, 1971 (absorbent pad for diapers and the like where the primary absorbent is a hydrophilic polyurethane foam sheet); U.S. Pat. No. 4,554,297 (Dabi), issued Nov. 19, 1985 (body fluid absorbing cellular polymers that can be used in diapers or catamenial products); U.S. Pat. No. 4,740,528 (Garvey et al), issued Apr. 26, 1988 (absorbent composite structures such as diapers, feminine care products and the like that contain sponge absorbents made from certain types of super-wicking, crosslinked polyurethane foams). U.S. Pat. No. 5,147,345 (Young et al.), issued Sep. 15, 1992, illustrates possible absorbent article configurations which are suitable for use with absorbent members formed of such polymeric foam materials, and is hereby incorporated herein by reference.

Although various polymeric foam materials have been suggested for use in absorbent articles, absorbent, open-celled polymeric foams have been developed which have the following desirable characteristics:

(a) a relatively greater affinity for absorbing body fluids than exhibited by other components in the absorbent article so that the foam material can drain (partition) fluids from these other components and keep the fluids stored within the foam structure;

(b) relatively good wicking and fluid distribution characteristics in order for the foam to transport the imbibed urine or other body fluid away from the initial impingement zone and into the unused balance of the foam structure, thus allowing for subsequent gushes of fluid to be accommodated; and (c) a relatively high storage capacity with a relatively high fluid capacity under load, i.e. under compressive forces.

As previously noted, a thinner absorbent core is usually a requirement for making relatively thin absorbent articles, such as diapers. However, providing absorbent polymeric foam materials that remain relatively thin in form until wetted with aqueous body fluids is not straightforward. The absorbent foam material needs to remain relatively thin during normal storage and use prior to being wetted. This relatively thin polymeric foam material must additionally have the needed absorbency characteristics described above if it is to be useful in high performance absorbent cores. Making relatively thin polymeric foams that are sufficiently soft and flexible for comfort of the wearer is also not a trivial task.

Relatively thin, collapsed (i.e. unexpanded), polymeric foam materials have been developed that, upon contact with aqueous body fluids, expand and absorb such fluids. These absorbent polymeric foam materials comprise a hydrophilic, flexible, nonionic polymeric foam structure of interconnected open-cells. Such collapsed polymeric foam materials remain relatively thin during normal shipping, storage and use conditions, until ultimately wetted with aqueous body fluids, at which point they expand. Because of their excellent absorbency characteristics, including capillary fluid transport capability, these collapsed polymeric foam materials are extremely useful in high performance absorbent cores for absorbent articles such as disposable diapers, adult incontinence pads or briefs, catamenial products such as sanitary napkins, disposable medical products such as bandages and dressings, and the like. Such collapsed polymeric foam materials are described in commonly assigned, co-pending U.S. patent application Ser. No. 07/989,270 (Dyer et al., filed Dec. 11, 1992), the disclosure of which is hereby incorporated herein by reference.

Although such polymeric foam materials exhibit superior storage capacity, and the advantageous thin-until-wet feature, they are often slower to acquire fluid than other materials. As a result, sudden gushes of fluid may simply run off of the surface of such an absorbent member with comparatively little fluid actually being absorbed and stored. This in turn may lead to premature product leakage before the absorbent capacity of the article is fully utilized. In addition, the use of comparatively thicker slices or additional layers of polymeric foam material to increase storage capacity increases the resulting stiffness of the absorbent article, without improving the acquisition rate.

Accordingly, it would be desirable to be able to make an absorbent member that: (1) has adequate or preferably superior acquisition characteristics, so as to be desirable in high performance absorbent cores used in absorbent articles such as disposable diapers, adult incontinence pads or briefs, catamenial products such as sanitary napkins, disposable medical products such as bandages and dressings, and the like; (2) is sufficiently flexible and soft so as to provide a high degree of comfort to the wearer of the absorbent article; (3) utilizes a combination of mechanical features and material properties to produce advantageous dynamic structures; and (4) can be manufactured on a commercial scale, at relatively reasonable or low cost.

DISCLOSURE OF THE INVENTION

The present invention relates to the use of slitted regions in absorbent members formed of absorbent materials having the ability to expand in at least one direction within the plane of the absorbent member when they absorb aqueous body fluids. More particularly, the present invention relates to the use of such slitted regions in absorbent members formed of relatively thin, collapsed (i.e. unexpanded), polymeric foam materials which have the capability of expanding in at least one direction within the plane of the absorbent member when they absorb aqueous body fluids. These absorbent polymeric foam materials preferably comprise a hydrophilic, flexible, polymeric foam structure of interconnected open-cells that, upon contact with aqueous body fluids, expands outwardly in all directions and absorbs such fluids. Importantly, with these foam materials the expansion process is reversible, and when fluid leaves the absorbent member due to evaporation or migration to other absorbent members the foam material at least partially collapses and is available to absorb the next potential discharge of fluid.

Compared with non-slitted regions of the absorbent member, slitted regions acquire fluid much faster due to the increased surface area provided by the edges of the slits. As the material expands, the surface area in the slitted region increases dramatically, and this increased surface area leads to a further increase in acquisition rate. The acquisition of more fluid leads to more expansion, and increased surface area, etc., until no more fluid is introduced or until the foam material reaches its fully expanded state, whichever first occurs.

Besides an enhanced acquisition rate, and increased flexibility, slitted regions undergoing fluid acquisition in combination with non-slitted and/or comparatively dryer surrounding regions and the planar expansion properties of the foam material enable the absorbent member to respond dynamically to various fluid loading conditions and generate beneficial structural features.

In one configuration, the deposition region of a polymeric foam absorbent member is provided with a plurality of slits to form a slitted region, while the perimeter of the absorbent member remains unslitted. The unslitted perimeter region also provides for greater structural integrity of the absorbent member during use by a wearer. When fluid is introduced into the absorbent member via the slitted region, the slitted region expands much more rapidly and to a greater extent than the surrounding unslitted region. The slitted region is constrained at its edges by the slower-to-expand unslitted region, and thus its continued expansion in the plane of the absorbent member forces it to deform and buckle outside of the plane of the absorbent member, forming at least one dome-like structure.

This doming effect causes the slits to open and the slit surfaces to displace angularly and/or translationally, at least partially exposing the slit surfaces to provide increased surface area for subsequent fluid discharges. The doming effect also creates a void space under the absorbent member which fluid can reach through the open slits. This void space provides temporary surge capacity for capturing and isolating excess fluid until it can be absorbed and stored by the absorbent member.

In another configuration, an absorbent member as described above is employed in fluid communication with an unslitted polymeric foam absorbent member in a multilayer configuration. When fluid is introduced into the deposition region of the slitted layer, the slitted layer performs as previously described. The unslitted layer then begins to acquire fluid from the slitted layer, and as this occurs the slitted layer begins to return to its collapsed state while the unslitted layer is expanding in the plane of the absorbent member. Due to restraining forces between the two layers which prevent sliding relative motion between them (provided that the layers are in direct contact or connected by an intermediate member which inhibits relative motion), the expanding unslitted layer causes the slits in the slitted layer to remain open and/or open further as the slitted layer collapses or partitions fluid to the unslitted layer. This effect is enhanced by the contraction in the planar direction of the individual strips of foam material between the slits.

The slit surfaces also acquire an advantageous funnel-like shape (compared with their usual straight-sided, parallel orientation), as opposed to being merely opened, which further enhances the ability of the absorbent member to rapidly acquire a subsequent discharge of fluid due to the exposure of the increased surface area to incoming fluid. This funnel-like shape is created due to contraction of the free surface of the slitted layer while the surface of the slitted layer in contact with the unslitted layer is restrained as it is held in contact with the unslitted layer, thus creating a strain differential within the slitted layer in a direction normal to the plane of the absorbent member.

In yet another configuration, the above funnel-like slit effect can be produced by performing the foam dewatering operation with the polymeric foam absorbent member adhered to a rigid substrate, or any other process by which the slits are formed into the funnel-like shape when the foam material is dry and ready for incorporation into an absorbent product. Absorbent members thus produced can then be incorporated into absorbent articles with the slits already pre-formed in an opened configuration to afford increased surface area for rapid fluid acquisition. Upon the acquisition of fluid, the slit surfaces approach each other and become more parallel as the foam material between the slits returns to its expanded state. The pre-formed funnel-like slit orientation is also particularly useful for containment and dewatering of moist or runny fecal material, as well as acquisition of higher viscosity fluids and/or those having a higher concentration of particulate material therein such as blood, menses, or wound fluids.

BRIEF DESCRIPTION OF THE DRAWINGS

The present invention will be better understood with reference to the following Detailed Description and to the accompanying Drawing Figures, in which.

DETAILED DESCRIPTION OF THE INVENTION

Figure 1:
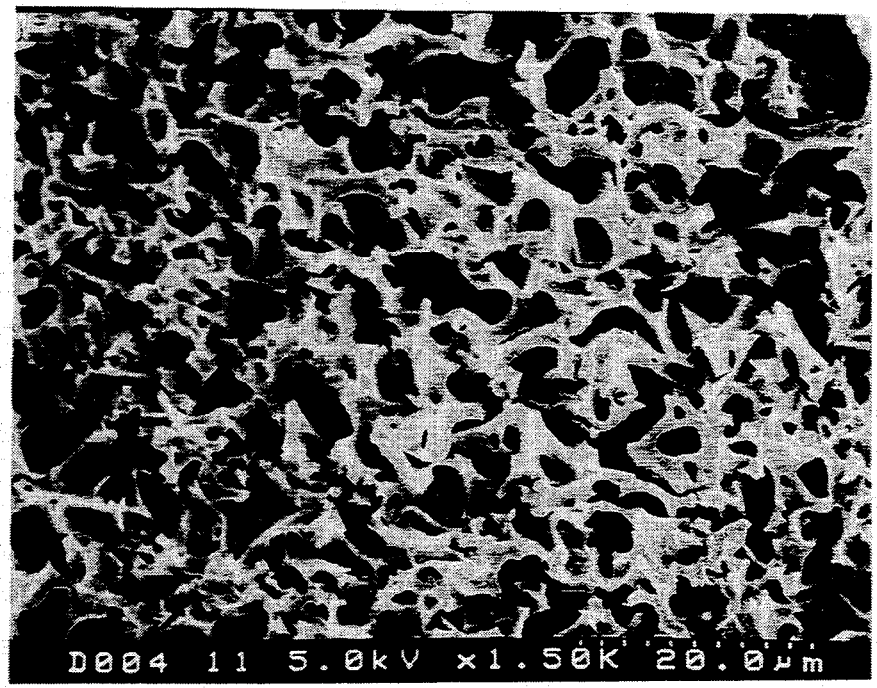
FIG. 1 of the drawings is a photomicrograph (1500× magnification) of an edge view of a cut section of a representative absorbent polymeric foam according to the present invention in its collapsed state.

While the principles of the present invention are applicable to absorbent members formed of any absorbent material having an interconnected network of open spaces which is capable of transporting aqueous body fluids within the absorbent member, and which expands upon acquisition of such fluids, a presently preferred material for use in accordance with the present invention is a polymeric foam material.

Polymeric foams of the type referred to herein can be characterized as the structures which result when a relatively monomer-free liquid is dispersed as droplets or "bubbles" in a polymerizable monomer-containing liquid, followed by polymerization of the monomers in the monomer-containing liquid which surrounds the droplets. The resulting polymerized dispersion can be in the form of a porous solidified structure which is an aggregate of cells, the boundaries or walls of which cells comprise solid polymerized material. The cells themselves contain the relatively monomer-free liquid which, prior to polymerization, had formed the droplets in the liquid dispersion.

Polymeric foams, including foams prepared from water-in-oil emulsions, can be relatively closed-celled or relatively open-celled in character, depending upon whether and/or the extent to which, the cell walls or boundaries, i.e., the cell windows, are filled with, or void of, polymeric material. The polymeric foam materials useful in the absorbent articles and structures of the present invention are those which are relatively open-celled in that the individual cells of the foam are for the most part not completely isolated from each other by polymeric material of the cell walls. Thus the cells in such substantially open-celled foam structures have intercellular openings or "windows" which are large enough to permit ready fluid transfer from one cell to the other within the foam structure.

In substantially open-celled structures of the type useful herein, the foam will generally have a reticulated character with the individual cells being defined by a plurality of mutually connected, three dimensionally branched webs. The strands of polymeric material which make up the branched webs of the open-cell foam structure can be referred to as "struts." Open-celled foams having a typical strut-type structure are shown by way of example in the photomicrograph set forth as FIG. 2. For purposes of the present invention, a foam material is "open-celled" if at least 80% of the cells in the foam structure that are at least 1 micron size are in fluid communication with at least one adjacent cell. Alternatively, a foam material can be considered to be substantially open-celled if it has a measured available pore volume that is at least 80% of the theoretically available pore volume, e.g., as determined by the water-to-oil weight ratio of the emulsion from which the foam material is formed.

In addition to being open-celled, the polymeric foam materials useful in the present invention are hydrophilic in character. The foams herein must be sufficiently hydrophilic to permit the foam to absorb aqueous body fluids in the amounts hereafter specified. As discussed hereafter with respect to preferred foam types and methods of foam preparation, the internal surfaces of the foam structures herein can be rendered hydrophilic by virtue of residual hydrophilizing agents left in the foam structure after polymerization or by virtue of selected post-polymerization foam treatment procedures which can be used to alter the surface energy of the material which forms the foam structure.

The extent to which polymeric foam structures such as those useful in the present invention are "hydrophilic" can be quantified by referencing the "adhesion tension" exhibited by such foams in contact with an absorbable test liquid. Adhesion tension is defined by the formula $$AT = \gamma \cos \Theta$$

wherein AT is adhesion tension in dynes/cm;
  $\gamma$ is the surface tension of a test liquid absorbed by the foam material in dynes/cm;
  $\Theta$ is the contact angle in degrees between the surface of the polymeric foam and the vector which is tangent to the test liquid at the point that the test liquid contacts the foam surface.

For any given hydrophilic foam material, the adhesion tension exhibited by the foam can be determined experimentally using a procedure whereby weight uptake of a test liquid, e.g., synthetic urine or propanol, is measured for a foam sample of known dimensions and capillary suction specific surface area. Such a procedure is described in greater detail in the TEST METHODS section of commonly assigned, co-pending U.S. patent application Ser. No. 07/989,270 (Dyer et al., filed Dec. 11, 1992), the disclosure of which is hereby incorporated herein by reference. The foams which are useful as absorbents in the present invention are generally those which have been rendered hydrophilic to the extent that they exhibit an adhesion tension of from about 15 to about 65 dynes/cm, more preferably from about 20 to about 65 dynes/cm, as determined by capillary suction uptake of synthetic urine having a surface tension of 65±5 dynes/cm.

The properties, features and/or characteristics of the polymeric foam materials useful in the present invention are somewhat interrelated and interdependent, but can be essentially categorized as follows: (I) those particularly relevant to its collapsed state; (II) those particularly relevant to its expanded state; (III) those equally relevant to either its collapsed or expanded state; and (IV) those particularly relevant to its absorbency when in contact with aqueous body fluids.

Correspondingly numbered Sections I–IV follow, explaining in greater detail the above-mentioned properties, features, and/or characteristics. Section V sets forth the features and characteristics provided by slitted regions in such absorbent members, and Section VI describes useful processes in preparing a presently preferred type of polymeric foam material. Finally, Examples are presented which set forth particular polymeric foam materials which have been found particularly useful in accordance with the present invention.

The following sections particularly pertain to a presently preferred variety of polymeric foam materials, although the principles set forth with particularity therein are applicable to other varieties of foam materials and other absorbent materials having similar expansion characteristics as well.

I. Collapsed State

The polymeric foam materials useful in the present invention are usually obtained by polymerizing a HIPE-type emulsion as described hereafter. These are water-in-oil emulsions having a relatively small amount of an oil phase and a relatively greater amount of a water phase. Accordingly, after polymerization, the resulting foam contains a substantial amount of water. This water can be expressed from the foam by compressive forces, and/or can be reduced by thermal drying, such as by heating in an oven, or by vacuum dewatering in conjunction with compressive forces. After compression, and/or drying, the polymeric foam material is in a three-dimensionally collapsed (or unexpanded) state.

Figure 2:
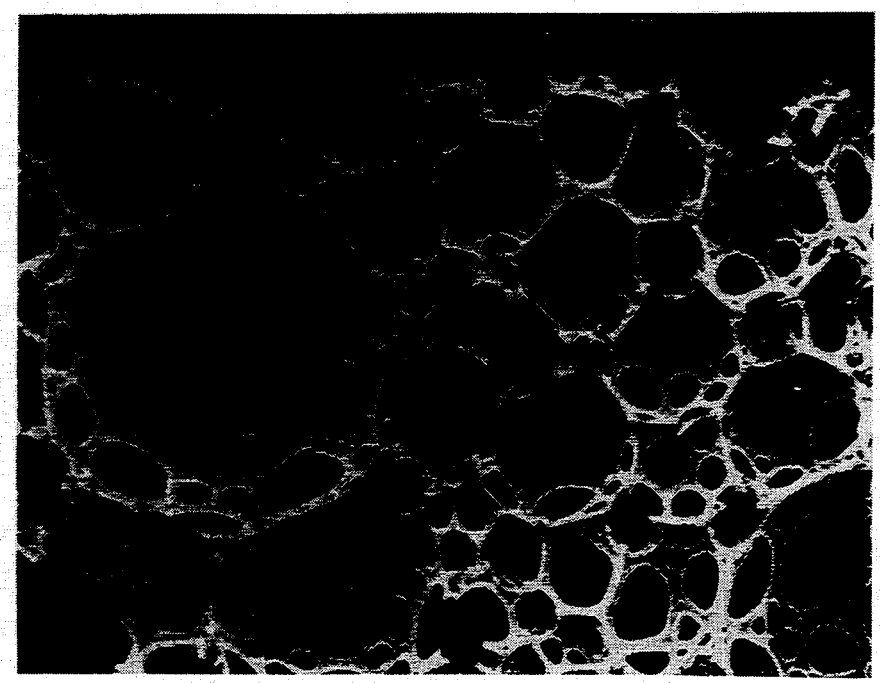
FIG. 2 of the drawings is a photomicrograph (1000× magnification) of a cut section of a representative absorbent polymeric foam according to the present invention in its expanded state.

The cellular structure of a representative collapsed HIPE foam from which water has been expressed by compression is shown in the photomicrograph set forth in FIG. 1. As shown in FIG. 1, the cellular structure of the foam is distorted, especially when compared to the HIPE foam structure shown in FIG. 2. (The foam structure shown in FIG. 2 is in its expanded state.) As can also be seen in FIG. 1, the voids or pores (dark areas) in the foam structure have been flattened or elongated. There is also no or minimal contact between adjacent struts of the foam structure.

Following compression and/or drying, the collapsed polymeric foam material can potentially re-expand, especially when wetted with aqueous body fluids. (See FIG. 2 which shows a typical HIPE foam structure useful in the present invention in its expanded state.) Surprisingly, these polymeric foam materials remain in this collapsed, or unexpanded state, for significant periods of time, e.g., up to at least about 1 year. The ability of these polymeric foam materials to remain in this collapsed/unexpanded state is believed to be due to the capillary forces, and in particular the capillary pressures developed within the foam structure. As used herein, "capillary pressure" refers to the pressure differential across the liquid/air interface due to the curvature of meniscus within the narrow confines of the pores in the foam. [See Chatterjee, "Absorbency," Textile Science and Technology, Vol. 7, 1985, p. 36.] For wetting liquids, this is essentially a pressure drop compared to atmospheric.

After compression and/or drying, the polymeric foam material useful in the present invention has residual water that includes both the water of hydration associated with the hydroscopic, hydrated salt incorporated therein (as described hereafter), as well as free water absorbed within the foam. It is this residual water (assisted by the hydrated salts) that is believed to exert capillary pressures on the resulting collapsed foam structure. Collapsed polymeric foam materials useful in the present invention can have residual water contents of at least about 4%, typically from about 4 to about 30%, by weight of the foam when stored at ambient conditions of 72° F. (22° C.) and 50% relative humidity. Preferred collapsed polymeric foam materials for use in the present invention have residual water contents of from about 5 to about 15% by weight of the foam.

In its collapsed state, the capillary pressures developed within the foam structure at least equal the forces exerted by the elastic recovery or modulus of the compressed polymer. In other words, the capillary pressure necessary to keep the collapsed foam material relatively thin is determined by the countervaling force exerted by the compressed polymeric foam as it tries to "spring back." The elastic recovery tendency of polymeric foams can be determined from stress-strain experiments where the expanded foam is compressed to about 25% of its original, expanded caliper (thickness) and then held in this compressed state until an equilibrium or relaxed stress value is measured. Alternatively, the equilibrium relaxed stress value is determined from measurements on the polymeric foam in its collapsed state when in contact with aqueous fluids, e.g., water. This alternative relaxed stress value is hereafter referred to as the "expansion pressure" of the foam. A detailed description of a procedure for determining the expansion pressure of foams is set forth in the TEST METHODS section of commonly assigned, co-pending U.S. patent application Ser. No. 07/989,270 (Dyer et al., filed Dec. 11, 1992), the disclosure of which is incorporated herein by reference.

The expansion pressure for polymeric foams useful in the present invention is about 30 kiloPascals (kPa) or less and typically from about 7 to about 20 kPa, i.e. the expansion pressure is within a relatively narrow range. This means the elastic recovery tendency of typical polymeric foams useful in the present invention is relatively constant. Accordingly, the capillary pressures necessary to provide collapsed, unexpanded polymeric foam materials useful in the present invention also typically fall within a constant range.

For purposes of the present invention, it has been found that the specific surface area per foam volume is particularly useful for empirically defining foam structures useful in the present invention that will remain in a collapsed state. A more detailed discussion of specific surface area per foam volume may be found in commonly assigned, co-pending U.S. patent application Ser. No. 07/989,270 (Dyer et al., filed Dec. 11, 1992), the disclosure of which is hereby incorporated herein by reference. As used herein, "specific surface area per foam volume" refers to the capillary suction specific surface area of the foam structure times the foam density. This specific surface area per foam volume value is characterized as "empirical" in that it is derived from (a) the capillary suction specific surface area which is measured during wetting of the dried foam structure, and (b) the density of the expanded foam structure after wetting to saturation, rather than by direct measurement of the dried, collapsed foam structure. Even so, it has been found that certain minimum specific surface area per foam volume values are correlatable to the ability of the foam structure to remain in a collapsed state. Polymeric foams useful in the present invention having specific surface area per foam volume values of at least about 0.025 $m^2$/cc, preferably at least about 0.05 $m^2$/cc, most preferably at least about 0.07 $m^2$/cc, have been found empirically to remain in a collapsed state.

Capillary suction specific surface area, foam density and cell size factors relevant to the capillary pressure and/or expansion pressure of the polymeric foam are discussed more fully hereafter.

A) Capillary Suction Specific Surface Area

Capillary suction specific surface area is, in general, a measure of the test-liquid-accessible surface area of the polymeric network forming a particular foam per unit mass of the bulk foam material (polymer structural material plus solid residual material). Capillary suction specific surface area is determined both by the dimensions of the cellular units in the foam and by the density of the polymer. Capillary suction specific surface area is thus a way of quantifying the total amount of solid surface provided by the foam network to the extent that such a surface participates in absorbency.

The capillary suction specific surface area is particularly relevant to whether adequate capillary pressures are developed within the foam structure to keep it in a collapsed state until wetted with aqueous body fluids. As discussed in greater detail in the above-mentioned commonly assigned, co-pending U.S. patent application Ser. No. 07/989,270 (Dyer et al., filed Dec. 11, 1992), the disclosure of which is incorporated herein by reference, the capillary pressure developed within the foam structure is proportional to the capillary suction specific surface area. Assuming other factors such as the foam density and adhesion tension of the fluid are constant, this means that, as the capillary suction specific surface area is increased (or decreased) the capillary pressure within the foam structure also increases (or decreases) proportionately.

For purposes of this invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the TEST METHODS section of commonly assigned, co-pending U.S. patent application Ser. No. 07/989,270 (Dyer et al., filed Dec. 11, 1992), the disclosure of which is incorporated herein by reference. Any reasonable alternative method for determining capillary suction specific surface area can also be utilized.

The collapsed open-celled, absorbent polymeric foams which are useful in the present invention are those that have a capillary suction specific surface area of at least about 0.3 m²/g. Typically, the capillary suction specific surface area is in the range from about 0.7 to about 8 m²/g, preferably from about 1 to about 7 m²/g, and most preferably from about 1.5 to about 6 m²/g. For pore volumes to be defined hereafter, hydrophilic foams having such capillary suction specific surface area values will generally possess an especially desirable balance of absorbent capacity, fluid-retaining and fluid-wicking or distribution characteristics for aqueous body liquids such as urine. In addition, foams having such capillary suction specific surface areas can develop a sufficient capillary pressure to keep the foam in a collapsed, unexpanded state until wetted with such aqueous body fluids.

B) Foam Density

Foam density in grams of foam per cubic centimeter of foam volume in air is specified herein on a dry basis. Thus the amount of absorbed aqueous liquid, e.g., residual salts and liquid left in the foam, for example, after HIPE emulsion polymerization, washing and/or hydrophilization, is disregarded in calculating and expressing foam density. Foam density as specified herein does include, however, other residual materials such as emulsifiers present in the polymerized foam. Such residual materials can, in fact, contribute significant mass to the foam material.

Any suitable gravimetric procedure which will provide a determination of mass of solid foam material per unit volume of foam structure can be used to measure foam density. For example, an ASTM gravimetric procedure described more fully in the TEST METHODS section of commonly assigned, co-pending U.S. patent application Ser. No. 07/989,270 (Dyer et al., filed Dec. 11, 1992, the disclosure of which is incorporated by reference) is one method which can be employed for density determination. For those situations where the foam sample preparation procedures (drying, aging, preflexing, etc.,) can inadvertently alter the density measurements obtained, then alternate density determination tests can also be utilized. Such alternative methods, for example, can include gravimetric density measurements using a test liquid absorbed within the foam material. This type of density determination method can be useful for characterizing very low density foams such as the foams herein wherein the dry density approximates the inverse of the pore volume of the foam. [See Chatterjee, "Absorbency," *Textile Science and Technology*, Vol. 7, 1985, p. 41.] As with capillary suction specific surface area, the ranges for foam density set forth hereafter are intended to be inclusive, i.e., they are intended to encompass density values that can be determined by any reasonable experimental test method.

The collapsed absorbent polymeric foams useful in the present invention have dry basis density values in the range of from about 0.05 to about 0.4 g/cm³, preferably from about 0.07 to about 0.25 g/cm³, and most preferably from about 0.1 to about 0.2 g/cm³. The density of the foam materials can be adjusted to within the foregoing ranges by controlling, in particular, the water-to-oil ratio of the HIPE emulsion.

C) Cell Size

An alternative feature which can be useful in defining preferred collapsed polymeric foam materials useful in this invention is cell size. Foam cells, and especially cells which are formed by polymerizing a monomer-containing oil phase that surrounds relatively monomer-free water-phase droplets, will frequently be substantially spherical in shape. The size or "diameter" of such substantially spherical cells is thus yet another commonly utilized parameter for characterizing foams in general as well as for characterizing certain preferred absorbent foam structures useful in the present invention. Since cells in a given sample of polymeric foam will not necessarily be of approximately the same size, an average cell size, i.e., average cell diameter, will often be specified.

A number of techniques are available for determining the average cell size of foams. These techniques include mercury porosimetry methods which are well known in the art. The most useful technique, however, for determining cell size in foams involves a simple measurement based on the scanning electron photomicrograph of a foam sample. FIG. 2, for example, shows a typical HIPE foam structure useful in the present invention in its expanded state. Superimposed on the photomicrograph is a scale representing a dimension of 20 microns. Such a scale can be used to determine average cell size via an image analysis procedure. Image analysis of photomicrographs of foam samples is, in fact, a commonly employed analytical tool which can be used to determine average cell size of the foam structures herein. Such a technique is described in greater detail in U.S. Pat. No. 4,788,225 (Edwards et al), issued Nov. 29, 1988, which is incorporated by reference.

The cell size measurements given herein are based on the number average cell size of the foam in its expanded state e.g., as shown in FIG. 2. The foams useful as absorbents for aqueous body fluids in accordance with the present invention will preferably have a number average cell size of about 50 microns or less and typically in the range of from about 5 to about 50 microns. More preferably, the number average cell size will be in the range from about 5 to about 40 microns, and most preferably from about 5 to about 35 microns.

II. Expanded State

A) Density Upon Saturation With Synthetic Urine

A particularly important property of the absorbent foams useful in the present invention in their expanded state is their density upon saturation with aqueous body fluids, relative to the dry basis density of the absorbent foam in its collapsed state. The density of the expanded foam when saturated with aqueous body fluids, relative to its dry basis density in its collapsed (compressed) state, provides a measure of the relative thickness of the foam in its expanded state. This provides a particularly relevant measure of how thin the foam is when expanded and when saturated with aqueous body fluids.

For the purposes of the present invention, the density of the absorbent foams in their expanded state is measured when it is saturated at 88° F. (31.1° C.) to its free absorbent capacity with synthetic urine having a surface tension of 65±5 dynes/cm. The density of the foam in its expanded state when saturated with the synthetic urine can be measured by a procedure described more fully in the Test Methods section of commonly assigned, co-pending U.S. patent application Ser. No. 07/989,270 (Dyer et al., filed Dec. 11, 1992), the disclosure of which is incorporated herein by reference. The density of the foam measured in its expanded, saturated state, is then related, as a percentage, to the dry basis density of the foam in its collapsed state. For the purposes of the present invention, the density of foams useful in the present invention in their expanded state upon saturation to their free absorbent capacity with synthetic urine can be in the range of from about 10 to about 50% of their dry basis density in their collapsed state, and is preferably in the range of from about 10 to about 30%, most preferably from about 15 to about 25%.

B) Pore Volume

Pore volume is a measure of the volume of the openings or cells in a porous foam structure per unit mass of solid material (polymer structure plus any residual solids) which forms the foam structure. Pore volume can be important in influencing a number of performance and mechanical features of the absorbent foams herein, especially in their expanded state. Such performance and mechanical features include absorbent capacity of the foams for aqueous body fluids, foam flexibility and foam compression deflection characteristics.

Pore volume can be determined by any suitable experimental method which will give an accurate indication of the actual pore volume of the structure. Such experimental methods will generally involve the measurement of the volume and/or mass of a test liquid which can be introduced into the foam structure and which therefore is representative of the volume occupied by the open cells of the foam. For this reason the pore volume parameter of the foams herein can also be referred to as "available pore volume."

One conventional way for determining available pore volume experimentally involves the introduction of a low surface tension, nonpolymer-swelling liquid such as 2-propanol into the foam structure. A procedure for determining available pore volume using 2-propanol is set forth in the TEST METHODS section of commonly assigned, co-pending U.S. patent application Ser. No. 07/989,270 (Dyer et al., filed Dec. 11, 1992), the disclosure of which is incorporated by reference. It should be understood, however, that alternative test liquids and procedures can also be used to determine available pore volume.

The foam materials useful in the present invention will generally have a pore volume of from about 12 to about 100 mL/g, more preferably from about 20 to about 70 mL/g, and most preferably from about 25 to about 50 mL/g.

C) Resistance to Compression Deflection

An important mechanical feature of the polymeric foams which are useful in this invention is the strength of the absorbent foam, in its expanded state, as determined by its resistance to compression deflection. The resistance to compression deflection exhibited by the foams herein is a function of the polymer elastic modulus and the density of the foam network. The polymeric elastic modulus is, in turn, determined by: a) the polymeric composition; b) the extent to which the polymeric foam is plasticized by residual material, e.g., emulsifiers, left in the foam structure after processing; and c) the conditions under which the foam was polymerized.

To be useful as absorbent structures in absorbent articles such as, for example, diapers, absorbent foam materials must be suitably resistant to deformation or compression by forces encountered when such absorbent materials are engaged in the absorption and retention of fluids. Foams which do not possess sufficient foam strength in terms of resistance to compression deflection may be able to acquire and store acceptable amounts of body fluid under no-load conditions, but will too easily give up such fluid under the compressive stress caused by the motion and activity of the wearer of the absorbent articles which contain the foam.

The resistance to compression deflection exhibited by the polymeric foams useful in the present invention can be quantified by determining the amount of strain produced in a sample of saturated foam material held under a certain confining pressure for a specified period of time. For the purposes of the present invention such measurements can be made on a foam sample of standard size (cylinders which are 0.25 cm thick and have a cross-sectional circular area of 6.5 $cm^2$). Such samples are saturated with synthetic urine having a surface tension of 65±5 dynes/cm and are thereafter subjected to a confining pressure of 5.1 kPa for a period of 15 minutes at a temperature of 88° F. (31.1° C.). The amount of strain produced in such testing is reported as a percentage of the saturated and fully expanded sample thickness that the compressed thickness of the sample represents. The method for carrying out this particular type of test for quantifying resistance to compression deflection is set forth in greater detail in the TEST METHODS section of commonly assigned, co-pending U.S. patent application Ser. No. 07/989,270 (Dyer et al., filed Dec. 11, 1992), the disclosure of which is incorporated by reference.

The absorbent foams useful herein are those which exhibit a resistance to compression deflection such that a confining pressure of 5.1 kPa produces a strain of typically from about 2 to about 80% compression of the foam structure when it has been saturated to its free absorbent capacity with synthetic urine having a surface tension of 65±5 dynes/cm. Preferably the strain produced under such conditions will be in the range from about 5 to about 40%, most preferably from about 5 to about 25%. For the preferred HIPE foams of this invention, resistance to compression deflection can be adjusted to strain values within the foregoing ranges by appropriate selection of monomer, comonomer and crosslinker types and concentrations in combination with the selection of appropriate emulsion formation and emulsion polymerization conditions and techniques. Thus, such preferred foams can be formed from materials with elastic modulii large enough to provide adequate resistance to compression deflection even though such foams are low density and have very fine struts.

D) Recovery From Compression Deflection

Recovery from compression deflection relates to the tendency or propensity of a piece of foam material to return to its original dimensions after being deformed or compressed under forces encountered in manufacture, storage or use. For purposes of the present invention, recovery from compression deflection of the preferred absorbent foams herein are determined on foams which are in their expanded state, and contain absorbed body fluid. Accordingly, recovery from compression deflection is measured on expanded foams which are saturated with synthetic urine.

A suitable procedure for determining recovery from compression deflection is set forth in the TEST METHODS section of commonly assigned, co-pending U.S. patent application Ser. No. 07/989,270 (Dyer et al., filed Dec. 11, 1992), the disclosure of which is incorporated by reference. Such a procedure in general involves compression and release of a standard size foam sample which has been saturated to its free absorbent capacity with synthetic urine. Samples are maintained under 50% compression for a set period of time and then are released from compression. The extent to which the sample recovers its thickness, in the presence of available free fluid, in the one-minute period after the release of compressive force is taken as a measure of the recovery from compression deflection (resilience) propensity of the sample.

Preferred absorbent foams useful in the present invention will generally exhibit a recovery of at least 75% of the expanded caliper when wet after one minute. More preferably, such preferred foam materials will have a recovery from compression deflection at least 80% when wet.

III. Collapsed or Expanded State

A) Flexibility

The absorbent foams useful in the present invention should be sufficiently flexible so that they can be utilized in absorbent products that will conform to the body shape of the wearer. Characterization of the absorbent foams herein as flexible, therefore, means that these foams can be deformed or bent to the extent necessary for use in such absorbent articles without significant damage to their structural integrity or significant loss of their absorbent properties.

Preferred absorbent foams for use in the present invention should also be sufficiently flexible to withstand compressive or deforming forces which are encountered during preparation, processing, packaging, shipping and storing of absorbent articles containing such foam materials. Disposable diapers, for example, are generally packaged and marketed in a folded condition wherein the diaper core is folded in both the longitudinal and transverse directions. Disposable diapers are also generally marketed in the form of stacks of folded diapers, which stacks are contained and compressed by their surrounding packaging. Accordingly, the compressive and deforming forces to which the foam absorbents herein can be subjected during processing and marketing can be even greater than those which are applied to the foam materials in use.

IV. Fluid Handling and Absorbency Characteristics

Absorbent foams having suitable polymeric compositions, and the structural characteristics and mechanical features as hereinbefore described, will in general exhibit especially desirable and useful body fluid handling and absorbency characteristics. Such fluid handling and absorbency characteristics are in turn the attributes of the preferred foam materials herein which render such foams especially suitable for use as absorbent structures in absorbent articles designed to acquire and hold aqueous body fluids.

The fluid handling and absorbency characteristics which are most relevant to the realization of suitable absorbent foams are: A) the free absorbent capacity of the foam; B) the rate of vertical wicking of fluid through the foam structure; and C) the absorbent capacity of the foam at specific reference wicking heights. Each of these characteristics is described in greater detail as follows:

A) Free Absorbent Capacity

Free absorbent capacity is the total amount of test fluid (synthetic urine) which a given foam sample will absorb into its cellular structure per unit mass of solid material in the sample. Such free absorbent capacity measurements are for purposes herein calculated at equilibrium, i.e., after the foam sample has been allowed to acquire and/or hold all of the fluid it can over whatever time period is needed to form a completely saturated foam sample with the test liquid. The foam materials which are especially useful as absorbent structures in absorbent articles such as diapers will at least meet a minimum free absorbent capacity.

Using the procedure described in greater detail in the TEST METHODS section of commonly assigned, co-pending U.S. patent application Ser. No. 07/989,270 (Dyer et al., filed Dec. 11, 1992, the disclosure of which is incorporated by reference), free absorbent capacity can both be determined for any given foam sample by a gravimetric analysis technique. In such a technique, a foam sample of specified known size and weight is placed in a dish of test fluid (synthetic urine) and is allowed to absorb the test fluid to equilibrium. After removal of the saturated sample from the fluid, the amount of fluid held per gram of foam, i.e., the measured free capacity, is then calculated. To be especially useful for absorbing urine in absorbent articles according to the present invention, absorbent foams should have a free capacity of at least about 12, and preferably at least about 20, mL of synthetic urine per gram of dry foam material.

B) Vertical Wicking Performance

Yet another fluid handling attribute of the absorbent foams useful herein relates to their ability to quickly move or "wick" acceptable amounts of body fluids through their foam structures. Vertical wicking, i.e., fluid wicking in a direction opposite from gravitational force, is an especially desirable performance attribute for the absorbent foam materials herein. This is because such materials will frequently be utilized in absorbent articles in a manner that fluid to be absorbed must be moved within the article from a relatively lower position to a relatively higher position within the absorbent core of the article.

Vertical wicking performance is related to the magnitude of the capillary suction driving force which moves liquid through the foam and holds it in the foam structure. Foam characterizing parameters which relate to vertical wicking propensity thus provide an indication as to how well preferred foams herein will perform as absorbent structures in absorbent articles. For the foam absorbents useful in the present invention, fluid wicking propensity can be quantified by referencing both a vertical wicking rate test and a vertical wicking absorbent capacity test.

1) Vertical Wicking Rate

The vertical wicking rate test measures the time taken for a colored test liquid (e.g., synthetic urine) from a reservoir to wick a vertical distance of 5 cm through a test strip of foam of specified size when the test is performed at 37° C. Such a vertical wicking rate test is described in greater detail in the TEST METHODS section of commonly assigned, co-pending U.S. patent application Ser. No. 07/989,270 (Dyer et al., filed Dec. 11, 1992), the disclosure of which is incorporated by reference. To be especially useful in absorbent articles for absorbing urine, the foam absorbents will preferably have a 5 cm vertical wicking rate of no more than about 30 minutes when wicking synthetic urine (65±5 dynes/cm). More preferably, the preferred foam absorbents for use in the present invention will have a 5 cm vertical wicking rate of no more than about 5 minutes when wicking synthetic urine.

2) Vertical Wicking Absorbent Capacity

The vertical wicking absorbent capacity test is carried out in conjunction with the vertical wicking rate test. Vertical wicking absorbent capacity measures the amount of test fluid per gram of absorbent foam that is wicked to each one inch (2.54 cm) vertical section of the same standard size foam sample used in the vertical wicking rate test. Such a determination is generally made after the sample has been allowed to vertically wick test fluid to equilibrium (e.g, after about 18 hours). Like the vertical wicking rate test, the vertical wicking absorbent capacity test is described in greater detail in the TEST METHODS section of commonly assigned, co-pending U.S. patent application Ser. No. 07/989,270 (Dyer et al., filed Dec. 11, 1992), the disclosure of which is incorporated by reference.

To be especially useful in absorbent articles for absorbing urine, preferred absorbent foams for use in the present invention will generally have a vertical wicking absorbent capacity such that, at 11.4 cm (4.5 inches) of vertical wicking height, the foam test strip wicks to at least about 50%, most preferably at about 75%, of its free absorbent capacity.

V. Slitted Regions

Of particular importance to the present invention is the inclusion of slitted regions within the polymeric foam absorbent member.

Figure 4:
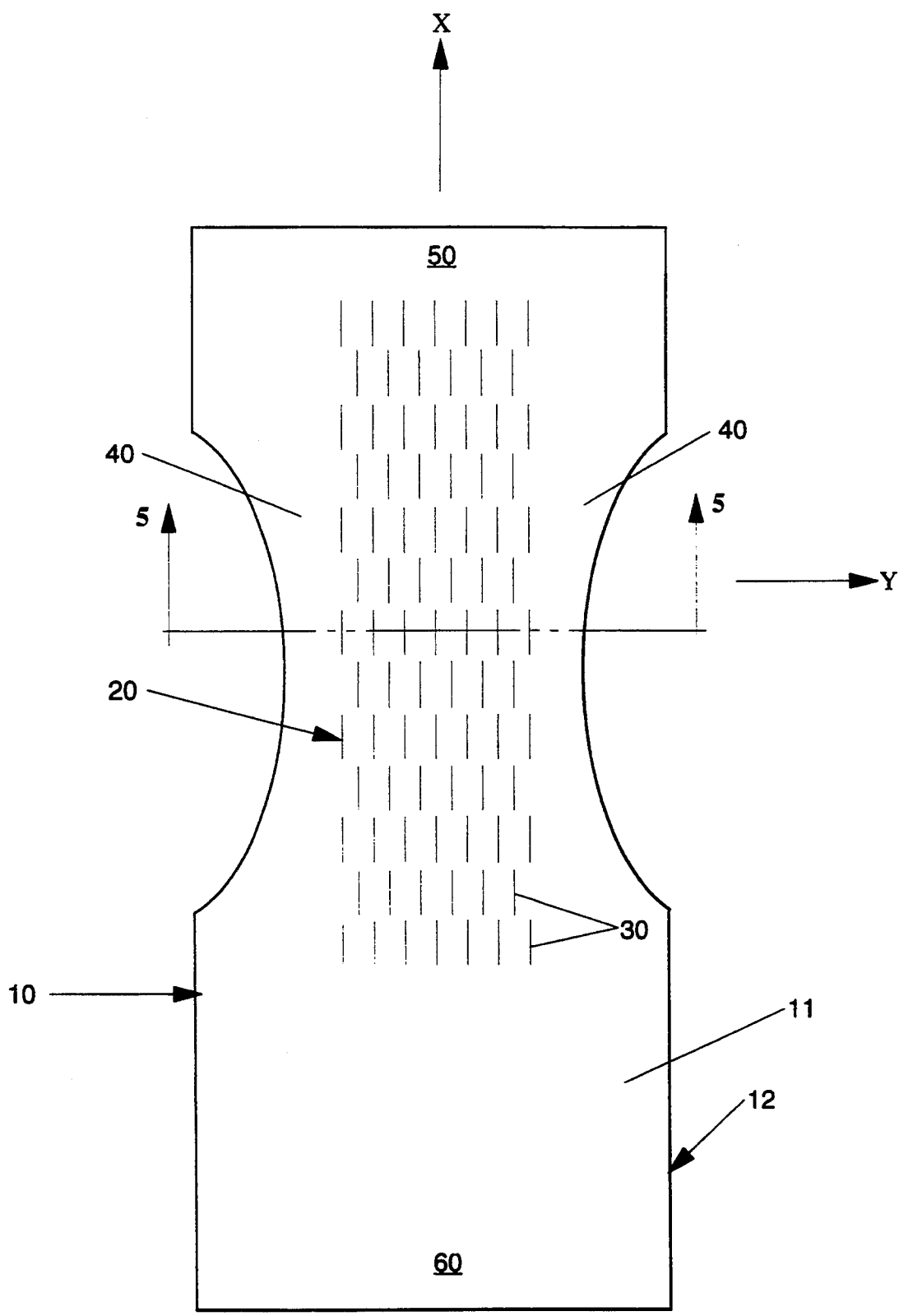
FIG. 4 is a plan view of an absorbent member according to a first embodiment of the present invention.

Improved polymeric foam material absorbent members according to the present invention incorporate a plurality of slits extending at least partially through the thickness of the absorbent member to form a slitted region. In a preferred configuration, such as depicted in FIG. 4 in the context of disposable diapers, the slitted region is located primarily in the typical deposition (crotch) region while an unslitted border of foam material surrounding this region is maintained. The slits can be formed when the foam material is in its dry, collapsed state, or while still in its expanded state prior to dewatering, and preferably extend entirely through the thickness of the material. The size of the slitted area may be varied as desired, and the slitting may be in any desired pattern, although the alternating "brickwork" pattern depicted in FIG. 4 is preferred.

The orientation of the slits plays a role in the migration of fluid within the absorbent member. The presently preferred pattern depicted in FIG. 4 maintains a relatively direct fluid path running in the X direction from the deposition region to both end regions of the absorbent member, and thus promotes more even fluid distribution and better utilization of the storage capacity of the foam material. On the contrary, slit orientations which are more Y direction oriented provide a more tortuous fluid path for fluid travelling in the X direction because the fluid must travel around the ends of each slit when the slit surfaces are displaced from one another.

FIG. 4 depicts an absorbent member 10 formed of polymeric foam material in a substantially moisture-free, collapsed condition which has been provided with a slitted region 20 according to the present invention. The slitted region 20 preferably includes a plurality of individual slits 30, and is preferably at least partially surrounded by an unslitted border region 40. End regions 50 and 60 are preferably unslitted as well. The slitted region 20 is preferably substantially confined to the region of typical liquid deposition when the absorbent member 10 is positioned in an absorbent article and worn by an individual, although it is within the scope of the present invention that at least part of the slitted region may fall outside of the typical deposition region or that a part of the deposition region may remain unslitted.

Also shown in FIG. 4 is the coordinate system defined by the absorbent member 10, which is suitable for use in a disposable diaper or adult incontinence article. The X direction depicted is the longitudinal direction which passes between the legs of the wearer from the end region 50 (near the front waist of the individual) to the end region 60 (near the rear waist of the individual). The Y direction depicted is the lateral direction which extends between the legs of the wearer from one side border 40 to the other. The Z direction is orthogonal to both the X and Y directions and is generally normal to the upper and lower surfaces 11 and 12, respectively, of the absorbent member 10.

Figure 5:
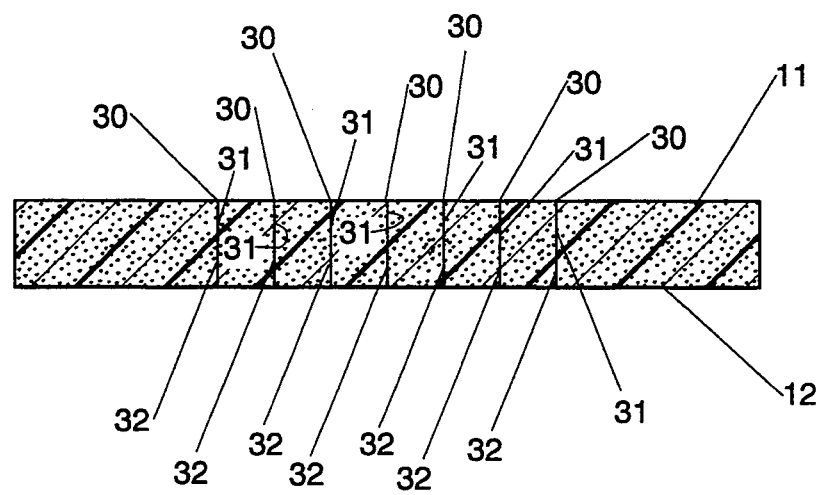
FIG. 5 is an elevational sectional view of the absorbent member of FIG. 4 taken along line 5—5.
Figure 6:
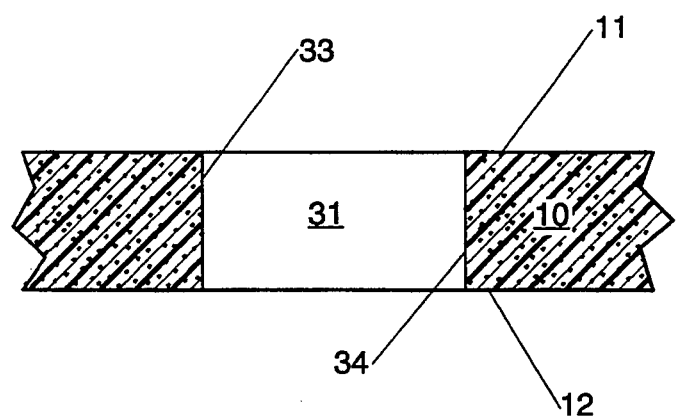
FIG. 6 is a fragmentary elevational sectional view of the absorbent member of FIG. 4, showing an individual slit.

As more clearly depicted in FIG. 5, which is a transverse sectional view of FIG. 4 taken along line 5—5, each individual slit 30 forms two slit surfaces 31 and 32. In a preferred configuration, the slits 30 extend entirely through the absorbent member 10 in a direction generally normal to its top and bottom surfaces 11 and 12, respectively. For a generally planar absorbent member such as depicted in FIG. 4, the slit surfaces 31 and 32 have a generally rectangular shape, defined at each end by the ends of the slit and on each side by the upper and lower surfaces 11 and 12, respectively, of the absorbent member 10. FIG. 6 is a fragmentary elevational sectional view of an absorbent member in the vicinity of an individual slit, illustrating a slit surface 31 bounded by slit ends 33 and 34 and the top and bottom surfaces 11 and 12, respectively.

When the absorbent member is in its collapsed, relatively moisture-free state, the slit surfaces of each individual slit are in close proximity to one another and are generally aligned with one another. Since no material is preferably removed from the absorbent member in the formation of the slits, in the absence of any forces applied to the absorbent member the slit surfaces are typically in contact with one another across substantially their entire surface area.

The deposition region of such an absorbent member typically correlates to the crotch region of a wearer during use. While the general outline of the periphery of the absorbent member in its unfolded and undeformed state is designed to at least partially accommodate the anatomical characteristics of a typical wearer, the use of slits in particular locations enables the absorbent member to better conform to the wearer's anatomical characteristics in those regions, particularly as the wearer moves about. This results in a more comfortable fit, as well as reduced leakage potential by minimizing .gaps in fit.

While the use of slits provides improved flexibility in the absorbent members, these slits also increase the effective surface area of the absorbent member. The surfaces of each slit contribute to the increase in surface area, particularly given increase in height of the slit surfaces due to the expansion of the absorbent member in the Z direction. This in turn provides an increase in the rate at which the absorbent member can acquire and store fluids. This acquisition rate increase is a matter of degree, and is highly dependent upon the material used for the foam absorbent member and other absorbent components (i.e., cellulose fibers, absorbent gelling materials, etc.), particularly those which play a role in initial fluid acquisition. The acquisition rate is also highly dependent upon the confining pressure (i.e., the external pressure) exerted upon the absorbent member when worn by a wearer under actual wearing conditions. With increased surface area, more fluid is acquired, which results in more expansion, etc. until the full storage capacity of the foam material is utilized.

In a substantially moisture-free condition, the open cellular structure of the foam material is in a collapsed state, and when infused with fluid the cellular structure returns to its expanded state, storing a comparatively large quantity of the fluid in the internal void spaces. This expansion property is directly tied to the acquisition of fluid, so regions that acquire fluid more quickly expand more quickly than regions which acquire fluid more slowly.

Besides an enhanced acquisition rate, and increased flexibility, slitted regions in combination with non-slitted and/or relatively drier surrounding regions enable the absorbent member to respond dynamically to various fluid loading conditions. The expansion property in the planar direction of the polymeric foam absorbent members preferred for use in the present invention thus provides an unexpected additional benefit in combination with the use of a slitted region in generating dynamic structural configurations which further enhance the fluid acquisition capabilities of the absorbent members.

Figure 7:
FIGS. 7 and 8 are elevational views (looking in the Y and X directions, respectively) of the absorbent member of FIG. 4 in a partially wetted condition.
Figure 8:
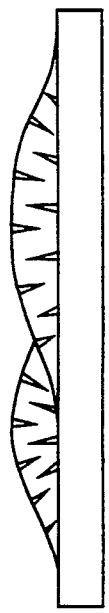
Figure 9:
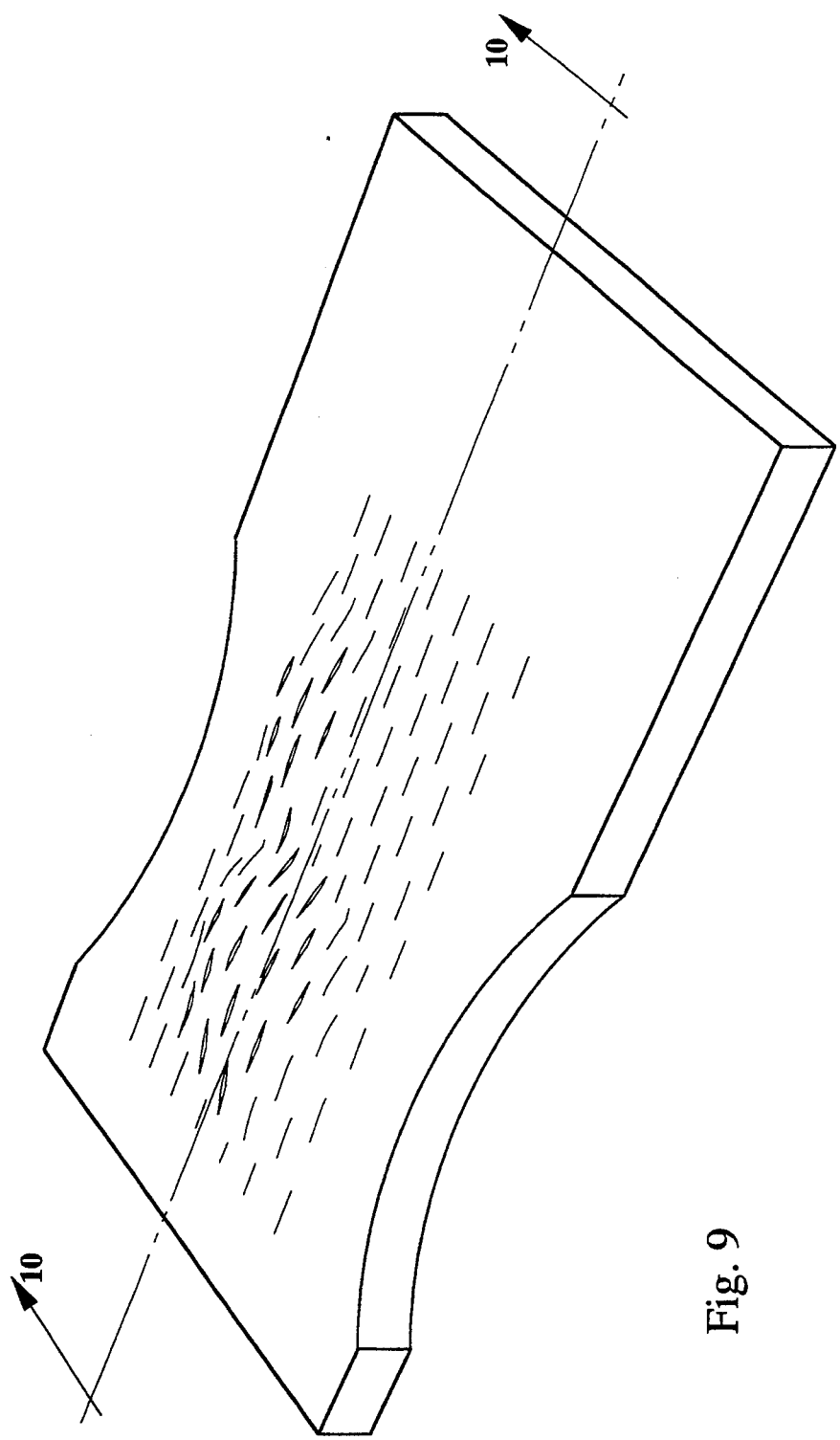
FIG. 9 is a perspective view of the absorbent member of FIG. 4 in a partially wetted condition.

FIGS. 7, 8, and 9 depict the absorbent member of FIG. 4 when it is in a partially fluid-loaded condition. When fluid is introduced into the deposition region, the slitted region expands in all three principal directions much more rapidly and to a greater extent than the surrounding unslitted region. Of particular importance is the ability of the preferred foam materials to expand in at least one direction in the plane of the absorbent member, and in this instance to expand in all directions within the plane of the absorbent member and also in the normal direction. The upper surface 11 and lower surface 12 are, in a preferred configuration, substantially parallel, and in such a condition the planar direction can be defined by reference to the general plane defined by either surface. If, however, the two surfaces are not substantially parallel, for purposes of the present invention the planar direction can be defined by a plane which can be constructed intermediate the general planes of the two respective surfaces. Once a planar direction is established by either method, a normal direction perpendicular to the planar direction is also correspondingly defined.

The slitted region is constrained at its edges by the slower-to-expand unslitted region, and thus its continued expansion forces it to deform and buckle out of the plane of the absorbent member to form one or more dome-like structures. This doming effect causes the slits to open and the slit surfaces to displace angularly and/or translationally, further exposing the slit surfaces to provide increased surface area for subsequent fluid discharges. The doming effect also creates a void space under the absorbent member which fluid can reach through the open slits. This void space provides temporary surge capacity for capturing and isolating excess fluid until it can be absorbed and stored by the absorbent member.

In the context of the present invention, by describing the slit surface displacement as "angular", the phenomenon intended to be described is the rotation of the slit surfaces from their generally parallel initial orientation to a substantially non-parallel orientation, producing what roughly approximates a funnel-like "V" or cup shape. This funnel-like shape provides an upwardly projecting exposed area for each slit surface, providing enhanced fluid acquisition capability. This shape formed by the slit surfaces increases the effectiveness of the slits in preventing fluids from running across the surface of the absorbent member, the slit edges thus slowing the fluid and permitting the foam material to capture it.

In like fashion, the phenomenon intended to be described by the use of the term "translational" displacement is the relative movement of the two slit surfaces of any particular individual slit from their initial orientation (wherein their top edges are generally coextensive and their bottom edges are generally coextensive) to an orientation wherein one top edge of one slit is somewhat higher than the other top edge, and likewise the one bottom edge of one slit is somewhat higher than the other bottom edge. This produces what may be roughly described as a "wicker"-type orientation, and provides for a laterally projecting exposed area for each slit surface, and in turn enhances fluid acquisition capability.

As fluid migrates into the surrounding regions of the absorbent member, and as these relatively drier regions tend to attract fluid away from the slitted and initially wetted region, the doming and slit displacement tend to diminish as the expansion of the surrounding regions approaches that of the slitted region. In fact, once the moisture content of the entire absorbent member is relatively uniform, the absorbent member returns to generally the configuration depicted in FIG. 4, albeit expanded in all directions.

Absorbent members according to the present invention may in fact have more than one slitted region, or may be slitted over substantially their entire surface. In this fashion, the slits may be utilized for their other beneficial characteristics such as improved flexibility.

In addition, depending upon the arrangement of the slits, more than one distorted or dome-like structure may be generated even within one slitted region (such as depicted in FIG. 9, wherein two such structures are illustrated), such that the absorbent member has an undulating shape which functions to more fully expose the slit surfaces.

The critical characteristic of the polymeric foam materials insofar as this dynamic structure is concerned is the ability of the foam to expand in at least one direction within the plane of the absorbent member. This may be described in terms of an expansion potential, in that the collapsed polymeric foam material has the potential to expand to a certain percentage beyond its collapsed size when loaded with fluid. Absorbent materials of the type presently preferred for use in the present invention will possess an expansion potential when fully loaded with fluid of at least about 5% if expansion potential only exists in one direction within the X-Y plane, and at least about 3% if the material has expansion potential in two or more directions within the X-Y plane. Such materials preferably have an expansion potential in the Z direction of at least 200%. More preferably, such materials have expansion potentials of at least about 10% in directions within the X-Y plane and at least about 300% in the Z direction when fully loaded with fluid. The presently preferred HIPE polymeric foam expands approximately 12% in the X direction (machine direction during manufacture), about 15% in the Y direction (cross direction during manufacture), and about 500% in the Z (thickness) direction when fully loaded with fluid.

Figure 10:
FIG. 10 is an elevational sectional view of the partially wetted absorbent member of FIG. 9 taken along line 10—10.

FIG. 10 is an elevational sectional view of the partially fluid-loaded absorbent member of FIG. 9. The point of view of FIG. 10 is substantially that of FIG. 7, with the section line 10—10 intersecting one of the dome-like structures of FIG. 9 (but not intersecting any individual slits). This Figure clearly depicts the expansion and buckling of the foam material which occurs in the slitted region in the area of fluid acquisition. It is the expansion and buckling such as depicted in FIG. 10 which produce the opening and displacement of the slit surfaces according to the present invention.

In general, expansion potential in a direction parallel to the direction of the slits produces the translational displacement phenomenon as a primary effect and may secondarily produce some angular displacement, while the expansion potential in a direction perpendicular to the direction of the slits produces the angular displacement phenomenon as a primary effect and may secondarily produce some translational displacement. In the foam materials which are presently preferred, the expansion potential in all directions, particularly both parallel to and perpendicular to the direction of the slits, produces both angular and translational displacement of slit surfaces in regions where the expansion is occurring during absorption of the aqueous body fluid. This combination of both angular and translational displacement provides an optimal configuration in terms of acquisition rate because it maximizes the surface irregularity and the surface area for acquisition.

As with the acquisition rate, the amount of deformation exhibited by absorbent members of the present invention is also highly dependent upon such factors as slit length, slit pattern, slit pattern density, sheet thickness, and the expansion properties and acquisition rate of the foam material itself. The area of fluid deposition and the presence or absence of an unslitted border may also influence the amount of deformations exhibited.

Figure 11:
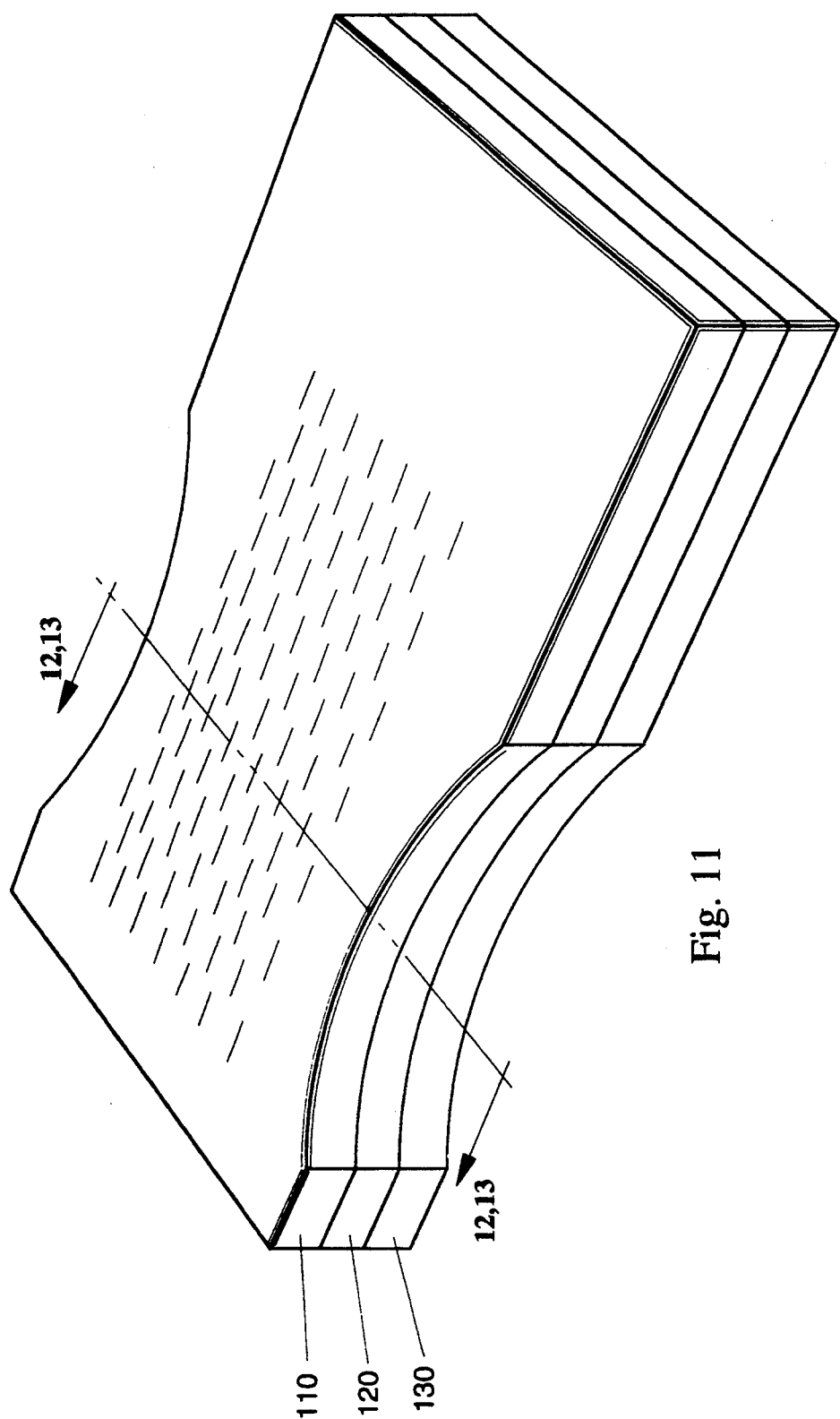
FIG. 11 is a perspective view of a multi-layered absorbent member according to a second embodiment of the present invention.

FIG. 11 depicts a multilayered embodiment of a slitted absorbent member according to the present invention, in which at least one layer comprises a layer of the polymeric foam material and incorporates a slitted region. The upper layer 110 in this illustration is provided with slitted and unslitted regions as described above. At least one of lower layers, in this illustration layers 120 and 130, is preferably not provided with slitted regions so as to provide a continuous surface below the slitted region(s) of the upper layer(s) and enhance the overall structural integrity of the absorbent member. While FIG. 11 depicts three layers having substantially the same size and shape, there may be more or less than three layers and the layers may be of differing sizes and/or shapes.

In multilayered configurations, the upper slitted layer performs substantially as described above insofar as initial fluid acquisition is concerned. In multilayered configurations which incorporate adjacent multiple layers of the polymeric foam material, once the upper layer has acquired fluid, the upper and adjacent layers interact to produce a unique and advantageous structural configuration. In multilayered configurations where only one layer is a foam material and the other layers do not have such expansion characteristics, the behavior of the foam layer is essentially similar to the single layer behavior described above.

As with most multilayered absorbent members, in which each layer itself has a propensity to acquire and store fluid, layers which have a lower moisture content will tend to draw fluid from layers which have a higher moisture content (a phenomenon commonly referred to as "partitioning"). In an absorbent member with layers having roughly the same absorbency characteristics, the fluid would tend to migrate throughout the layers of the absorbent member until a roughly equal fluid distribution is achieved throughout the absorbent member.

The uppermost layer (or whichever layer is located in proximity to the source of the body fluid) typically has a higher moisture content, at least initially, than the next lower layer, thus establishing a moisture gradient downward through the absorbent member. The next lower layer will thus tend to draw fluid from the uppermost layer through their contacting surface areas in order to achieve an equilibrium between layers with respect to moisture content.

Due to the unique abilities of the polymeric foam materials which are preferred in accordance with the present invention, the foam material in layers which are acquiring fluid will be expanding while the foam material in layers which are giving up fluid will be contracting. In addition, the surfaces of the polymeric foam material tend to have a comparatively high coefficient of friction when wetted, and the surfaces tend to be drawn together by capillary forces. As such, when adjacent surfaces of adjacent layers are moistened, relative sliding movement between layers is greatly reduced.

Figure 12:
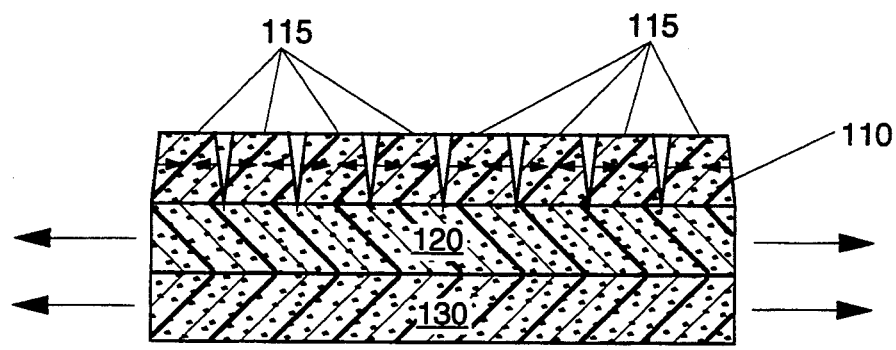
FIGS. 12 and 13 are elevational sectional views of the absorbent member of FIG. 11 in a partially wetted condition taken along lines 12—12 and 13—13, respectively.

As shown in FIG. 12, which is a cross-sectional view of the absorbent member of FIG. 11, these properties of the polymeric foam material generate a beneficial structural configuration when multiple layers of collapsed polymeric foam materials are used. Forces exerted on various regions of the foam material are depicted by the smaller arrows in FIG. 12, and as shown the lower layers 120 and 130 tend to expand outwardly (in all three directions, actually) while the uppermost layer 110 is contracting with its corresponding loss of fluid to the next lower layer 120. Since the bottom surface of layer 110 and the upper surface of layer 120 cannot move relative to one another due to the above-described friction/capillary suction phenomenon, the outwardly expanding layer 120 tends to hold open or further pull open the slits of the uppermost layer 110, as shown in FIG. 12. This effect is enhanced by the contraction of the individual strips of foam material 115 between the slits and at the edges of the uppermost layer. The funnel-like shape occurs due to contraction of the free surface of the slitted layer while the surface of the slitted layer in contact with the unslitted layer is restrained as it is held in contact with the unslitted layer, thus creating a strain differential within the slitted layer in a direction normal to the plane of the absorbent member.

Figure 13:
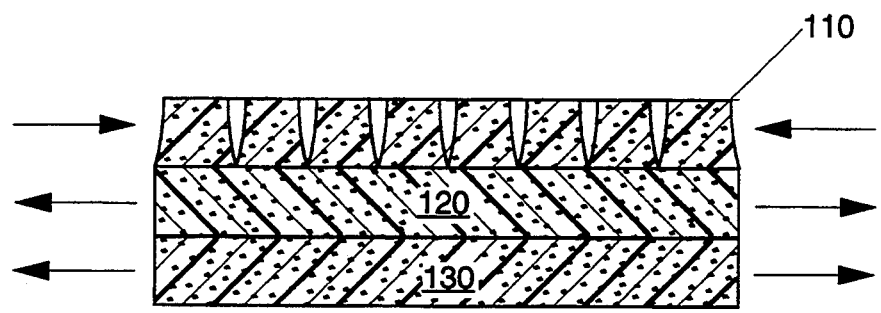

Indeed, as the foam material in the uppermost layer 110 continues to contract relative to the next lower layer 120, the sidewalls of the slits tend to become more curved into a cup-like shape, as depicted in FIG. 13. This cup-like structure is particularly advantageous in that the slit surfaces remain exposed for subsequent liquid discharges and act as funnels to direct fluid into the slits and downward toward the underlying layers. This structure is also advantageous in the context of containing and dewatering moist or runny fecal material, as such material will also be directed downward into the slits rather than being allowed to run laterally over the surface of the absorbent member.

Figure 15:
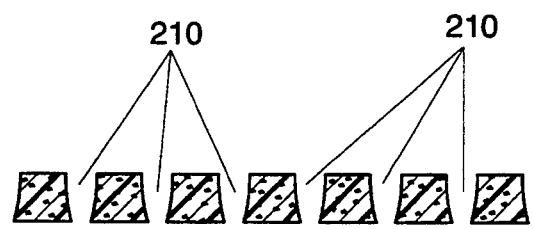
FIG. 15 is an elevational sectional view similar to FIG. 5 of the absorbent member of FIG. 14.
Figure 14:
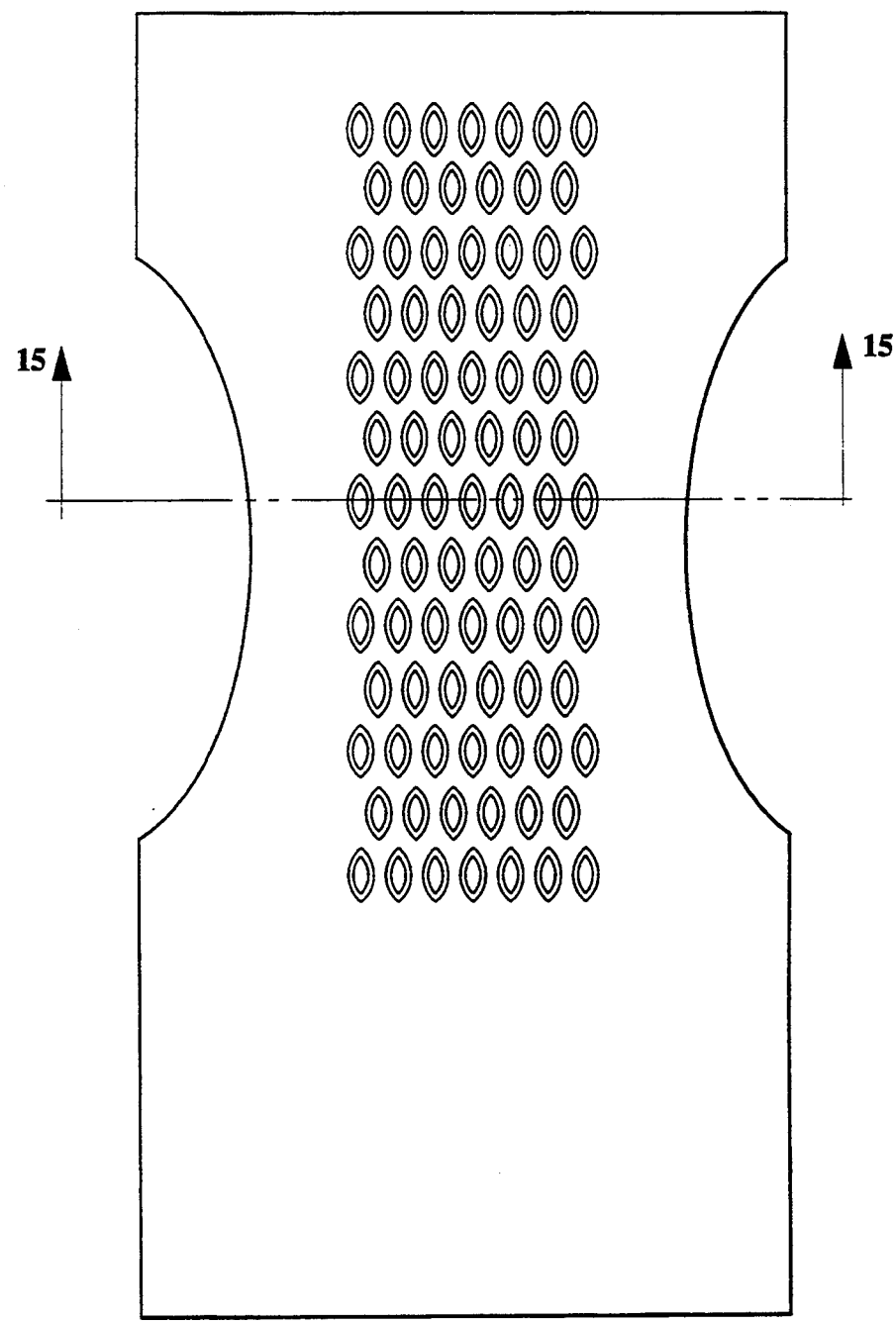
FIG. 14 is a plan view of an absorbent member according to a third embodiment of the present invention.
Figure 16:
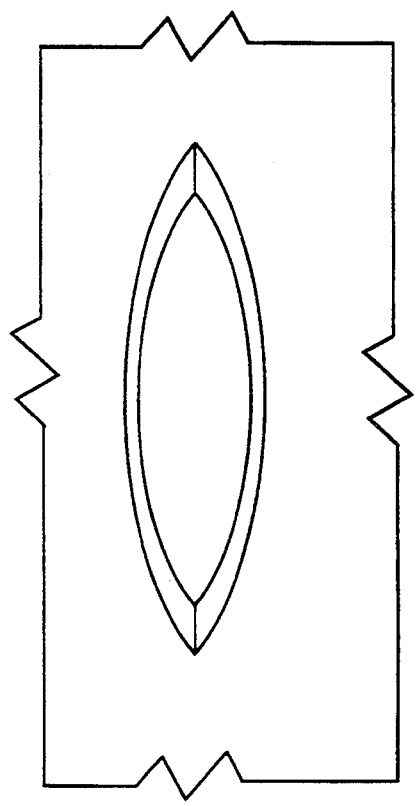
FIG. 16 is a fragmentary plan view of the absorbent member of FIG. 14, presenting a magnified view of one individual slit in its preformed state.

This advantageous cup-like shape can in fact be formed during the process of making the absorbent member, such that single layers of foam material can exhibit this structural configuration even prior to fluid acquisition. FIG. 15 is a cross-sectional view similar to FIG. 5, and illustrates such a pre-formed single sheet of polymeric foam material with the slits formed into an open cup-like configuration and indicated by the numeral 210. FIG. 14 is a plan view of such an absorbent member, and FIG. 16 is a fragmentary plan view of the absorbent member of FIG. 14 presenting a magnified view of one individual slit in its preformed state.

In preparing such an absorbent member, the slits are preferably cut into the foam material prior to the dewatering process. The foam material is then dewatered, preferably via air and/or thermal drying, with the lower surface adhered to a flat, non-porous substrate. Alternatively, the material could be dewatered, the slits formed in the substantially moisture-free foam material, and the material then re-hydrated, after which the dewatering process in conjunction with the substrate would proceed similarly. In a wetted condition, the lower surface will not slide on the substrate due to the high coefficient of friction of the wet foam and capillary suction. As the foam material dries and contracts, the lower surface retains its closed-slit orientation because the surface cannot contract while in contact with the substrate. The upper surface in contrast contracts freely with the loss of fluid, and the individual strips of foam material between slits contract. The resulting difference in contraction between the upper and lower surfaces of the absorbent member becomes "locked in" once the foam material is thoroughly dried, and it can then be peeled up from the substrate for further processing.

The pre-formed cup-like shape thus presents the surfaces of the pre-opened slits for the first discharge of fluid and/or deposit of fecal material, and the increased surface area in comparison with the conventionally slitted absorbent members provides an improved acquisition rate. Once the absorbent member acquires fluid, and the moisture distribution within the absorbent member equalizes (in a single layer context), the slits will tend to lose their cup-like shape and return generally to the configuration shown in FIG. 4.

These pre-formed slit configurations are particularly useful for containment and dewatering of moist or runny fecal material, as well as acquisition of higher viscosity fluids and/or those having a higher concentration of particulate material therein such as blood, menses, or wound fluids. The open cup-like regions function as receptacles for capturing such materials and retaining them while the moisture they contain is absorbed into the foam material. These pre-formed slits also reduce the tendency of fluids to run off of the surface of the foam material by providing a surface with large openings into which the fluid penetrates via the upper opening.

In a multi-layer configuration, such pre-formed slits may also afford immediate fluid access to the next underlying layer (in configurations wherein the slits are substantially opened from upper surface to lower surface) while still maintaining a comparatively high degree of surface area exposed to the incoming fluid. This permits the underlying layer to begin acquiring fluid immediately and directly rather than via partitioning action from the uppermost layer, and hence further improves the overall acquisition rate of the absorbent member.

In multilayer embodiments, one or more layers of the absorbent members may comprise some material other than polymeric foam, such as a more conventional absorbent material. Such layers of other materials may be utilized as an acquisition layer over one or more layers of foam material having slitted region(s) and/or as a storage layer underlying such layer(s) of foam material having slits. Such materials may also be utilized between the layers of foam material. Some materials which may be suitable include cellulose fibers, modified cellulose fibers, rayon, polyester fibers such as polyethylene terephthalate (DACRON), hydrophobic nylon (HYDROFIL), and the like. Absorbent structures formed from thermally bonded, airlaid cellulosic fibrous materials may also be utilized. Along with such fibrous materials, absorbent gelling materials in particulate or sheet form may also be desirable. The use of slits may also be advantageous for absorbent gelling materials in sheet form for enhanced fluid acquisition.

Figure 17:
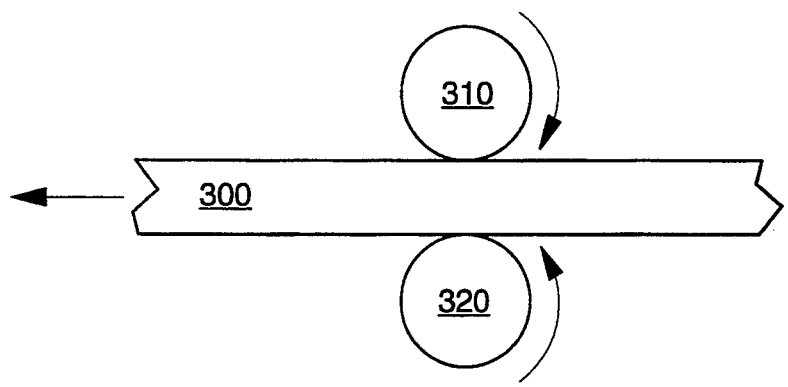
FIGS. 17 and 18 schematically illustrate two possible methods of forming slitted regions in absorbent members according to the present invention.
Figure 18:
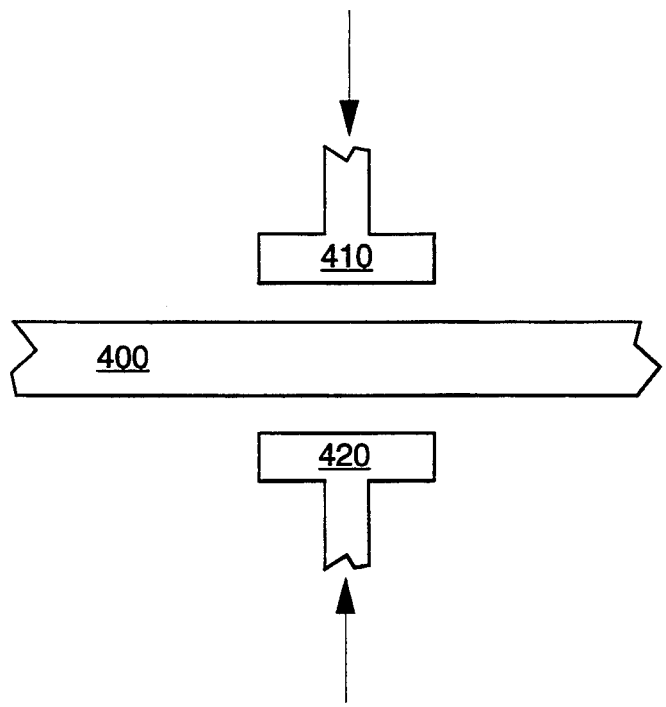

FIGS. 17 and 18 schematically illustrate two possible methods of forming slitted regions in sheets of polymeric foam materials. In FIG. 17, the sheet of foam material 300 is passed between a knife roll 310 and an anvil roll 320. The knife roll 310 includes a series of small, sharp knife blades in the desired pattern and spacing, and these blades cut through the foam material when it is compressed between the two rolls to form the slitted region. FIG. 18 depicts a stamping operation in which a die 410 including a series of small, sharp knife blades in the desired pattern and spacing and an anvil 420 are brought together to capture and compress a foam sheet 400. The blades on the die thus cut through the foam material to form the slitted region. Other processes utilizing, for example, individual or sequential knives or similar devices may also be employed.

With respect to each of the foregoing embodiments, it is presently preferred that the slits extend entirely through the absorbent member, although at least some of the advantages of the present invention may be obtained if the slits only extend partially through the thickness of the absorbent member.

It is also possible to form grooves or channels in the absorbent member rather than slits, but the use of slits is presently preferred to minimize the amount of material loss which may accompany the grooving process and retain full absorbent capacity.

The overall shape and/or size of the absorbent member may be tailored as desired for specific applications, and the overall shape and/or size of the slitted region(s) may also be adjusted as desired.

In the design of the slitted region, other performance aspects may be considered, such as in-use integrity of the absorbent member, flexibility, and elasticity/stretch considerations. Slit length, pattern density, and slit orientation are all characteristics which may be adjusted to optimize overall performance of the absorbent member in terms of acquisition rate and mechanical performance.

The degree of deformation in single and multilayer contexts, and the amount of cupping experienced in preparation of preformed open slits, are all influenced by slit length, slit pattern density, sheet thickness, and material properties. In general, thinner sheet thicknesses are believed to reduce the level of dynamic effects exhibited due to the corresponding reduction in foam material per unit area and the reduction in strain differential between upper and lower surfaces. Higher density patterns in general are believed to reduce the amount of displacement and the degree of cupping exhibited. Shorter slit lengths are also believed to reduce the displacements and the amount of cupping exhibited. Materials exhibiting slower expansion rates generally result in slower dynamic responses, and materials having less expansion potential in the plane of the structure generally exhibit less dynamic response than materials having greater expansion potentials.

In the area of preforming the slits in the open configuration, the temperature at which the dewatering operation is accomplished is also believed to be an important consideration. If it is accomplished at or below ambient temperatures the resulting structure appears to be generally stiffer, and thus does not as easily collapse to form the pre-opened slits in the cup-like configuration. If the operation is carried out at higher temperatures, for example at 100 degrees F., the polymer structure typically remains softer and more compliant, and thus more readily forms the pre-opened slits in the cup-like configuration.

While absorbent members according to the present invention may be utilized separately, i.e., without accompanying structures, for use in absorbing aqueous body fluids such absorbent members are preferably incorporated into some sort of absorbent article. As such, the absorbent article in general will comprise one or more absorbent members according to the present invention and some sort of backing sheet having means for affixing the absorbent article onto a wearer so as to maintain the deposition region of the absorbent member in proximity to the source of the aqueous body fluid. In a preferred type of absorbent article, the backing sheet will have a substantially liquid impervious character so as to protect clothing, bedding, etc. from contact with the wetted absorbent member.

Absorbent members according to the present invention have been found to be particularly well suited for use in absorbent articles in the form of disposable articles and adult incontinence garments. In this context, a presently preferred form of absorbent article for use with absorbent members according to the present invention is presented by the previously referenced U.S. Pat. No. 5,147,345 (Young et al.), issued Sep. 15, 1992, which is incorporated by reference.

VI. Preparation of Collapsed Polymeric Foam Materials

As previously noted, collapsed polymeric foam materials useful in the present invention can be prepared by polymerization of certain water-in-oil emulsions having a relatively high ratio of water phase to oil phase. Emulsions of this type which have these relatively high water to oil phase ratios are commonly known in the art as high internal phase emulsions ("HIPEs" or "HIPE" emulsions). The polymeric foam materials which result from the polymerization of such emulsions are referred to herein as "HIPE foams."

The relative amounts of the water and oil phases used to form the HIPE emulsions are, among many other parameters, important in determining the structural, mechanical and performance properties of the resulting polymeric foams. In particular, the ratio of water to oil in the foam-forming emulsion can influence the foam density, cell size, and capillary suction specific surface area of the foam and dimensions of the struts which form the foam. The emulsions used to prepare these presently preferred HIPE foams will generally have water-to-oil phase ratios ranging from about 12:1 to about 100:1, more preferably from about 20:1 to about 70:1, and most preferably from about 25:1 to about 50:1.

A. Oil Phase Components

The continuous oil phase of the HIPE emulsion comprises monomers that are polymerized to form the solid foam structure. This monomer component includes a "glassy" monomer, a "rubbery" comonomer and a cross-linking agent. Selection of particular types and amounts of monofunctional monomer(s) and comonomer(s) and polyfunctional cross-linking agent(s) can be important to the realization of absorbent HIPE foams having the desired combination of structure, mechanical, and fluid handling properties which render such materials suitable for use in the invention herein.

The monomer component utilized in the oil phase of the HIPE emulsions comprises one or more monofunctional monomers that tend to impart glass-like properties to the resulting polymeric foam structure. Such monomers are referred to as "glassy" monomers, and are, for purposes of this invention, defined as monomeric materials which would produce high molecular weight (greater than 6000) homopolymers having a glass transition temperature, $T_g$, above about 40° C. These monofunctional glassy monomer types include methacrylate-based monomers (e.g., methyl methacrylate) and styrene-based monomers (e.g., styrene). The preferred monofunctional glassy monomer type is a styrene-based monomer with styrene itself being the most preferred monomer of this kind. Substituted, e.g., monosubstituted, styrene such as p-methylstyrene can also be employed. The monofunctional glassy monomer will normally comprise from about 5 to about 40%, more preferably from about 10 to about 30%, more preferably from about 15 to about 25%, and most preferably about 20%, by weight of the monomer component.

The monomer component also comprises one or more monofunctional comonomers which tend to impart rubber-like properties to the resulting polymeric foam structure. Such comonomers are referred to as "rubbery" comonomers and are, for purposes of this invention, defined as monomeric materials which would produce high molecular weight (greater than 10,000) homopolymers having a glass transition temperature, $T_g$, of about 40° C. or lower. Monofunctional rubbery comonomers of this type include, for example, the $C_4$–$C_{12}$ alkylacrylates, the $C_6$–$C_{14}$ alkylmethacrylates, and combinations of such comonomers. Of these comonomers, n-butylacrylate and 2-ethylhexylacrylate are the most preferred. The monofunctional rubbery comonomer will generally comprise from about 30 to about 80%, more preferably from about 50 to about 70%, and most preferably from about 55 to about 65%, by weight of the monomer component.

Since the polymer chains formed from the glassy monomer(s) and the rubbery comonomer(s) are to be cross-linked, the monomer component also contains a polyfunctional cross-linking agent. As with the monofunctional monomers and comonomers, selection of a particular type and amount of cross-linking agent is very important to the eventual realization of preferred polymeric foams having the desired combination of structural, mechanical, and fluid-handling properties.

Depending upon the type and amounts of monofunctional monomers and comonomers utilized, and depending further upon the desired characteristics of the resulting polymeric foams, the polyfunctional cross-linking agent can be selected from a wide variety of polyfunctional, preferably difunctional, monomers. Thus, the cross-linking agent can be a divinyl aromatic material such as divinylbenzene, divinyltolulene or diallylphthalate. Alternatively, divinyl aliphatic crosslinkers such as any of the diacrylic or dimethylacrylic acid esters of polyols, such as 1,6-hexanediol and its homologues, can be utilized. The cross-linking agent found to be suitable for preparing the preferred HIPE emulsions herein is divinylbenzene. The cross-linking agent of whatever type will generally be employed in the oil phase of the foam-forming emulsions herein in an amount of from about 10 to about 40%, more preferably from about 15 to about 25%, and most preferably about 20%, by weight of the monomer component.

Another essential component of the oil phase is an emulsifier which permits the formation of stable HIPE emulsions. Such emulsifiers are those which are soluble in the oil phase used to form the emulsion. Emulsifiers utilized are typically nonionic and include the sorbitan fatty acid esters, the polyglycerol fatty acid esters, and combinations thereof. Preferred emulsifiers include sorbitan laurate (e.g., SPAN® 20), sorbitan oleate (e.g., SPAN® 80), combinations of sorbitan laurate and sorbitan palmirate (e.g., SPAN® 40) in a weight ratio of from about 1:1 to about 3:1, and especially combinations of sorbitan laurate with certain polyglycerol fatty acid esters to be described hereafter.

The oil phase used to form the HIPE emulsions will generally comprise from about 67 to about 98% by weight monomer component and from about 2 to about 33% by weight emulsifier component. Preferably, the oil phase will comprise from about 80 to about 95% by weight monomer component and from about 5 to about 20% by weight emulsifier component.

In addition to the monomer and emulsifier components, the oil phase can contain other optional components. One such optional oil phase component is an oil soluble polymerization initiator of the general type hereafter described. Another possible optional component of the oil phase is a substantially water insoluble solvent for the monomer and emulsifier components. A solvent of this type must, of course, not be capable of dissolving the resulting polymeric foam. Use of such a solvent is not preferred, but if such a solvent is employed, it will generally comprise no more than about 10% by weight of the oil phase.

B. Water Phase Components

The discontinuous internal phase of the HIPE emulsions is the water phase which will generally be an aqueous solution containing one or more dissolved components. One essential dissolved component of the water phase is a water-soluble electrolyte. The dissolved electrolyte in the water phase of the HIPE emulsion serves to minimize the tendency of monomers and crosslinkers which are primarily oil soluble to also dissolve in the water phase. This, in turn, is believed to minimize the extent to which, during polymerization of the emulsion, polymeric material fills the cell windows at the oil/water interfaces formed by the water phase droplets. Thus, the presence of electrolyte and the resulting ionic strength of the water phase is believed to determine whether and to what degree the resulting preferred polymeric foams can be open-celled.

Any electrolyte which provides ionic species to impart ionic strength to the water phase can be used. Preferred electrolytes are mono-, di-, or tri-valent inorganic salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in foam materials presently preferred for use in the present invention. Generally the electrolyte will be utilized in the water phase of the HIPE emulsions in a concentration in the range of from about 0.2 to about 20% by weight of the water phase. More preferably, the electrolyte will comprise from about 1 to about 10% by weight of the water phase.

The HIPE emulsions will also typically contain a polymerization initiator. Such an initiator component is generally added to the water phase of the HIPE emulsions and can be any conventional water-soluble free radical initiator. Materials of this type include peroxygen compounds such as sodium, potassium and ammonium persulfates, hydrogen peroxide, sodium peracetate, sodium percarbonate and the like. Conventional redox initiator systems can also be utilized. Such systems are formed by combining the foregoing peroxygen compounds with reducing agents such as sodium bisulfite, L-ascorbic acid or ferrous salts.

The initiator material can comprise up to about 5 mole percent based on the total moles of polymerizable monomers present in the oil phase. More preferably, the initiator comprises from about 0.001 to 0.5 mole percent based on the total moles of polymerizable monomers in the oil phase. When used in the water-phase, such initiator concentrations can be realized by adding initiator to the water phase to the extent of from about 0.02% to about 0.4%, more preferably from about 0.1% to about 0.2%, by weight of the water phase.

C. Hydrophilizing Agents and Hydratable Salts

The cross-linked polymer material that forms the preferred collapsed absorbent foam structures herein will preferably be substantially free of polar functional groups on its polymeric structure. Thus, immediately after the polymerization step, the polymer material which forms the foam structure surfaces of such preferred absorbent foams will normally be relatively hydrophobic in character. Accordingly, preferred just-polymerized foams can need further treatment to render the foam structure surfaces relatively more hydrophilic so that such foams can be used as absorbents for aqueous body fluids. Hydrophilization of the foam surfaces, if necessary, can generally be accomplished by treating the polymerized HIPE foam structures with a hydrophilizing agent in a manner described more fully hereafter.

Hydrophilizing agents are any materials which will enhance the water wettability of the polymeric surfaces with which they are contacted and onto which they are deposited. Hydrophilizing agents are well known in the art, and can include surfactant materials, preferably of the nonionic type. Hydrophilizing agents will generally be employed in liquid form, and can be dissolved or dispersed in a hydrophilizing solution which is applied to the HIPE foam surfaces. In this manner, hydrophilizing agents can be adsorbed onto the polymeric surfaces of the preferred HIPE foam structures in amounts suitable for rendering such surfaces substantially hydrophilic but without altering the desired flexibility and compression deflection characteristics of the foam. In preferred foams which have been treated with hydrophilizing agents, the hydrophilizing agent is incorporated into the foam structure such that residual amounts of the agent which remain in the foam structure are in the range from about 0.5% to about 20%, preferably from about 5 to about 12%, by weight of the foam.

One type of suitable hydrophilizing agent is a nonirritating oil-soluble surfactant. Such surfactants can include all of those previously described for use as the emulsifier for the oil phase of the HIPE emulsion, such as sorbitan laurate (e.g., SPAN ® 20), and combinations of sorbitan laurate with certain polyglycerol fatty acid esters to be described hereafter. Such hydrophilizing surfactants can be incorporated into the foam during HIPE emulsion formation and polymerization or can be incorporated by treatment of the polymeric foam with a solution or suspension of the surfactant dissolved or dispersed in a suitable carrier or solvent.

Another material that needs to be incorporated into the HIPE foam structure is a hydratable, and preferably hygroscopic or deliquesent, water soluble inorganic salt. Such salts include, for example, toxicologically acceptable alkaline earth metal salts. Materials of this type and their use in conjunction with oil-soluble surfactants as the foam hydrophilizing agent is described in greater detail in the PCT Published Application WO 93/04113, published Mar. 4, 1993. This application was filed in the name of The Procter & Gamble Company, and the disclosure of this publication is hereby incorporated herein by reference. Preferred salts of this type include the calcium halides such as calcium chloride which, as previously noted, can also be employed as the electrolyte in the water phase of the HIPE emulsions used to prepare the polymeric foams.

Hydratable inorganic salts can easily be incorporated into the polymeric foams herein by treating the foams with aqueous solutions of such salts. Solutions of hydratable inorganic salts can generally be used to treat the foams after completion of, or as part of, the process of removing the residual water phase from the just-polymerized foams. Contact of foams with such solutions is preferably used to deposit hydratable inorganic salts such as calcium chloride in residual amounts of at least about 0.1% by weight of the foam, and typically in the range of from about 0.1 to about 8%, preferably from about 3 to about 6%, by weight of the foam.

Treatment of preferred foam structures which are relatively hydrophobic as polymerized with hydrophilizing agents (with or without hydratable salts) will typically be carried out to the extent that is necessary and sufficient to impart suitable hydrophilicity to the preferred HIPE foams of the present invention. Some foams of the preferred HIPE emulsion type, however, can be suitably hydrophilic as prepared and can have incorporated therein sufficient amounts of hydratable salts, thus requiring no additional treatment with hydrophilizing agents or hydratable salts. In particular, such preferred HIPE foams can be those wherein sorbitan fatty acid esters such as sorbitan laurate (e.g., SPAN 20), or combinations of sorbitan laurate with certain polyglycerol fatty acid esters to be described hereafter, are used as emulsifiers added to the oil phase and calcium chloride is used as an electrolyte in the water phase of the HIPE emulsion. In that instance, the residual-emulsifier-containing internal polymerized foam surfaces will be suitably hydrophilic, and the residual water-phase liquid will contain or deposit sufficient amounts of calcium chloride, even after the polymeric foams have been dewatered.

D. Processing Conditions for Obtaining HIPE Foams

Foam preparation for foams presently preferred for use in the present invention typically involves the steps of: 1) forming a stable high internal phase emulsion (HIPE); 2) polymerizing/curing this stable emulsion under conditions suitable for forming a solid polymeric foam structure; 3) washing the solid polymeric foam structure to remove the original residual water phase from the polymeric foam structure and, if necessary, treating the polymeric foam structure with a hydrophilizing agent and/or hydratable salt to deposit any needed hydrophilizing agent/hydratable salt, and 4) thereafter dewatering this polymeric foam structure (preferably including compression in the z-direction) to the extent necessary to provide a collapsed, unexpanded polymeric foam material useful as an absorbent for aqueous body fluids.

To consistently obtain relatively thin, collapsed polymeric foam materials useful in the present invention, it has been found to be particularly important to carry out the emulsion formation and polymerization steps in a manner such that coalescence of the water droplets in the HIPE emulsion is reduced or minimized. HIPE emulsions are not always stable, particularly when subjected to higher temperature conditions to effect polymerization and curing. As the HIPE emulsion destabilizes, the water droplets present in it can aggregate together, and coalesce to form much large water droplets. Indeed, during polymerization and curing of the emulsion, there is essentially a race between solidification of the foam structure, and coalescence of the water droplets. An appropriate balance has to be struck such that coalescence of the water droplets is reduced, yet polymerization and curing of the foam structure can be carried out within a reasonable time. (While some coalescence can be tolerated if the remaining water droplets are very small in size, such nonuniform cell sizes in the resulting foam can adversely affect the fluid transport properties of the foam, especially its wicking rate.)

Reduction in the coalescence of water droplets in the HIPE emulsion leads to a smaller average cell size in the resulting foam structure after polymerization and curing. It is believed that this resulting smaller average cell size in the polymeric foam material is a key mechanism behind consistent formation of relatively thin, collapsed polymeric foam materials presently preferred for use in the present invention. (Uniformly small cell sizes in the resulting foam are also believed to lead to good absorbency, and especially fluid transport (e.g., wicking) characteristics.) The number average cell size of the polymeric foam materials is about 50 microns or less and is typically in the range from about 5 to about 50 microns, preferably from about 5 to about 40 microns, and most preferably from about 5 to about 35 microns, when prepared under conditions that reduce coalescence of water droplets in the HIPE emulsion. Techniques for consistently reducing coalescence of water droplets in the HIPE emulsion will be discussed in greater detail in the following description of the emulsion formation and polymerization/curing steps for obtaining collapsed polymeric foams:

1. Formation of HIPE Emulsion

The HIPE emulsion is formed by combining the oil phase components with the water phase components in the previously specified weight ratios. The oil phase will contain the previously specified essential components such as the requisite monomers, comonomers, crosslinkers and emulsifiers, and can also contain optional components such as solvents and polymerization initiators. The water phase used will contain the previously specified electrolytes as an essential component and can also contain optional components such as water-soluble emulsifiers, and/or polymerization initiators.

The HIPE emulsion can be formed from the combined oil and water phases by subjecting these combined phases to shear agitation. Shear agitation is generally applied to the extent and for a time period necessary to form a stable emulsion from the combined oil and water phases. Such a process can be conducted in either batchwise or continuous fashion and is generally carried out under conditions suitable for forming an emulsion wherein the water phase droplets are dispersed to such an extent that the resulting polymeric foam will have the requisite pore volume and other structural characteristics. Emulsification of the oil and water phase combination will frequently involve the use of a mixing or agitation device such as a pin impeller.

One preferred method of forming HIPE emulsions which can be employed herein involves a continuous process for combining and emulsifying the requisite oil and water phases. In such a process, a liquid stream comprising the oil phase is formed and provided at a flow rate ranging from about 0.08 to about 1.5 mL/sec. Concurrently, a liquid stream comprising the water phase is also formed and provided at a flow rate ranging from about 4 to about 50 mL/sec. At flow rates within the foregoing ranges, these two streams are then combined in a suitable mixing chamber or zone in a manner such that the requisite water to oil phase weight ratios as previously specified are approached, reached and maintained.

In the mixing chamber or zone, the combined streams are generally subjected to shear agitation as provided, for example, by a pin impeller of suitable configuration and dimensions. Shear will typically be applied to the extent of from about 1000 to about 2500 sec.$^{-1}$. Residence times in the mixing chamber will frequently range from about 5 to about 30 seconds. Once formed, the stable HIPE emulsion in liquid form can be withdrawn from the mixing chamber or zone at a flow rate of from about 4 to about 52 mL/sec. This preferred method for forming HIPE emulsions via a continuous process is described in greater detail in U.S. Pat. No. 5,149,720 (DesMarais et al), issued Sep. 22, 1992, which is incorporated by reference.

In consistently reducing the coalescence of the water droplets present in the HIPE emulsion, it is particularly preferred to use certain types of emulsifier systems in the oil phase, especially if the HIPE emulsion is to be polymerized or cured at temperatures above about 50° C. These preferred emulsifier systems comprise a combination of sorbitan laurate (e.g., SPAN® 20), and certain polyglycerol fatty acid esters (PGEs) as co-emulsifiers. The weight ratio of sorbitan laurate to PGE is usually within the range of from about 10:1 to about 1:10. Preferably, this weight ratio is in the range of from about 4:1 to about 1:1.

The PGEs especially useful as co-emulsifiers with sorbitan laurate are usually prepared from polyglycerols characterized by high levels of linear (i.e., acyclic) diglycerols, reduced levels of tri- or higher polyglycerols, and reduced levels of cyclic diglycerols. Suitable polyglycerol reactants (weight basis) usually have a linear diglycerol level of at least about 60% (typical range of from about 60 to about 90%), a tri- or higher polyglycerol level of no more than about 40% (typical range of from about 10 to about 40%), and a cyclic diglycerol level of no more than about 10% (typical range of from 0 to about 10%). Preferably, these polyglycerols have a linear diglycerol level of from about 60 to about 80%, a tri- or higher polyglycerol level of from about 20 to about 40%, and a cyclic diglycerol level of no more than about 10%. (A method for determining the polyglycerol distribution is set forth in the PGE ANALYTICAL METHODS section of commonly assigned, co-pending U.S. patent application Ser. No. 07/989,270 (Dyer et al., filed Dec. 11, 1992), the disclosure of which is hereby incorporated herein by reference.)

PGEs especially useful as co-emulsifiers with sorbitan laurate are also prepared from fatty acid reactants characterized by fatty acid compositions having high levels of combined $C_{12}$ and $C_{14}$ saturated fatty acids, and reduced levels of other fatty acids. Suitable fatty acid reactants have fatty acid compositions where the combined level of $C_{12}$ and $C_{14}$ saturated fatty acids is at least about 40% (typical range of from about 40 to about 85%), the level of $C_{16}$ saturated fatty acid is no more than about 25% (typical range of from about 5 to about 25%), the combined level of $C_{18}$ or higher saturated fatty acids is no more than about 10% (typical range of from about 2 to about 10%), the combined level of $C_{10}$ or lower fatty acids is no more than about 10% (typical range of from about 0.3 to about 10%), the balance of other fatty acids being primarily $C_{18}$ monounsaturated fatty acids. Preferably, the fatty acid composition of these fatty acid reactants is at least about 65% combined $C_{12}$ and $C_{14}$ saturated fatty acids (typical range of from about 65 to about 75%), no more than about 15% $C_{16}$ saturated fatty acid (typical range of from about 10 to about 15%), no more than about 4% combined $C_{18}$ or higher saturated fatty acids (typical range of from about 2 to about 4%), and no more than about 3% $C_{10}$ or lower fatty acids (typical range of from about 0.3 to about 3%). (A method for determining the fatty acid composition is set forth in the PGE ANALYTICAL METHODS section of commonly assigned, co-pending U.S. patent application Ser. No. 07/989,270 (Dyer et al., filed Dec. 11, 1992), the disclosure of which is incorporated by reference.)

PGEs useful as co-emulsifiers with sorbitan laurate are also usually characterized as imparting a minimum oil/water interfacial tension (IFT), where the oil phase contains monomers used in the HIPE emulsion and the water phase contains calcium chloride. Suitable PGE co-emulsifiers usually impart a minimum oil/water IFT of at least about 0.06 dynes/cm, with a typical range of from about 0.06 to about 1.0 dynes/cm. Especially preferred PGEs impart a minimum oil/water IFT of at least about 0.09 dynes/cm, with a typical range of from about 0.09 to about 0.3 dynes/cm. (A method for measuring the IFT of these PGEs is set forth in the PGE ANALYTICAL METHODS section of commonly assigned, co-pending U.S. patent application Ser. No.

07/989,270 (Dyer et al., filed Dec. 11, 1992), the disclosure of which is incorporated by reference.)

PGEs useful as coemulsifiers with sorbitan monolaurate can be prepared by methods well known in the art. See, for example, U.S. Pat. No. 3,637,774 (Babayan et al), issued Jan. 25, 1972, and Mcintyre, "Polyglycerol Esters," J. Am. Oil Chem. Soc., Vol. 56, No. 11 (1979), pp. 835A–840A, which are incorporated by reference and which describe methods for preparing polyglycerols and converting them to PGEs. PGEs are typically prepared by esterifying polyglycerols with fatty acids. Appropriate combinations of polyglycerols can be prepared by mixing polyglycerols obtained from commercial sources or synthesized using known methods, such as those described in U.S. Pat. No. 3,637,774. Appropriate combinations of fatty acids can be prepared by mixing fatty acids and/or mixtures of fatty acids obtained from commercial sources. In making PGEs useful as co-emulsifiers, the weight ratio of polyglycerol to fatty acid is usually from about 50:50 to 70:30, preferably from about 60:40 to about 70:30.

Typical reaction conditions for preparing suitable PGE co-emulsifiers involve esterifying the polyglycerols with fatty acids in the presence of 0.1–0.2% sodium hydroxide as the esterification catalyst. The reaction is initiated at atmospheric pressure at about 210°–220° C., under mechanical agitation and nitrogen sparging. As the reaction progresses, the free fatty acids diminish and the vacuum is gradually increased to about 8 mm Hg. When the free fatty acid level decreases to less than about 0.5%, the catalyst is then neutralized with a phosphoric acid solution and the reaction mixture rapidly cooled to about 60° C. This crude reaction mixture can then be subjected to settling or other conventional purification steps (e.g., to reduce the level unreacted polyglycerol) to yield the desired PGEs.

2. Polymerization/Curing of the HIPE Emulsion

The HIPE emulsion formed will generally be collected or poured in a suitable reaction vessel, container or region to be polymerized or cured. In one embodiment herein, the reaction vessel comprises a tub constructed of polyethylene from which the eventually polymerized/cured solid foam material can be easily removed for further processing after polymerization/curing has been carried out to the extent desired. It is usually preferred that the temperature at which the HIPE emulsion is poured into the vessel be approximately the same as the polymerization/curing temperature.

Polymerization/curing conditions to which the HIPE emulsion will be subjected will vary depending upon the monomer and other makeup of the oil and water phases of the emulsion, especially the emulsifier systems used, and the type and amounts of polymerization initiators utilized. Frequently, however, polymerization/curing conditions will comprise maintenance of the HIPE emulsion at elevated temperatures above about 30° C., more preferably above about 35° C., for a time period ranging from about 4 to about 24 hours, more preferably from about 4 to about 18 hours.

In reducing coalescence of water droplets in the HIPE emulsion, it is particularly preferred to carry out the polymerization/curing at relatively lower temperatures, especially if the preferred combination of sorbitan laurate and PGE co-emulsifiers is not used in preparing the HIPE emulsion. In these situations, suitable lower polymerization/curing temperatures are in the range of from about 30° to about 50° C., preferably from about 35° to about 45° C., and most preferably about 40° C. If polymerization/curing is carried out at temperatures much above about 50° C., the thermal stress on the emulsion can cause the water droplets present to aggregate and coalesce, thus forming much larger cells in the resulting polymeric foam, especially if the preferred combination of sorbitan laurate and PGE co-emulsifiers is not used in preparing the HIPE emulsion. This can lead to polymeric foams that cannot remain in a collapsed, unexpanded state after dewatering.

A bulk solid polymeric foam is typically obtained when the HIPE emulsion is polymerized/cured in a reaction vessel, such as a tub. This bulk polymerized HIPE foam is typically cut or sliced into a sheet-like form. Sheets of polymerized HIPE foam are easier to process during subsequent treating/washing and dewatering steps, as well as to prepare the HIPE foam for use in absorbent articles. The bulk polymerized HIPE foam is typically cut/sliced to provide a cut caliper in the range of from about 0.08 to about 2.5 cm. During subsequent dewatering, this typically leads to collapsed HIPE foams having a caliper in the range of from about 0.008 to about 1.25 cm.

3. Treating/Washing HIPE Foam

The solid polymerized HIPE foam which is formed will generally be a flexible, open-cell porous structure having its cells filled with the residual water phase material used to prepare the HIPE emulsion. This residual water phase material, which generally comprises an aqueous solution of electrolyte, residual emulsifier, and polymerization initiator, should be at least partially removed from the foam structure at this point prior to further processing and use of the foam. Removal of the original water phase material will usually be carried out by compressing the foam structure to squeeze out residual liquid and/or by washing the foam structure with water or other aqueous washing solutions. Frequently several compressing and washing steps, e.g., from 2 to 4 cycles, will be utilized.

After the original water phase material has been removed from the foam structure to the extent required, the HIPE foam, if needed, can be treated, e.g., by continued washing, with an aqueous solution of a suitable hydrophilizing agent and/or hydratable salt. Hydrophilizing agents and hydratable salts which can be employed have been previously described and include sorbitan laurate (e.g., SPAN 20) and calcium chloride. As noted, treatment of the HIPE foam structure with the hydrophilizing agent/hydratable salt solution continues, if necessary, until the desired amount of hydrophilizing agent/hydratable salt has been incorporated and until the foam exhibits a desired adhesion tension value for any test liquid of choice.

4. Foam Dewatering

After the HIPE foam has been treated/washed to the extent necessary to render the eventually dried foam suitably hydrophilic, and optionally to incorporate a sufficient amount of a hydratable salt, preferably calcium chloride, the foam will generally be dewatered. Dewatering can be brought about by compressing the foam (preferably in the z-direction) to squeeze out residual water, by subjecting the foam, or the water therein, to elevated temperatures, e.g., thermal drying at temperatures from about 60° C. to about 200° C., or to microwave treatment, by vacuum dewatering or by a combination of compression and thermal drying/microwave/vacuum dewatering techniques. The dewatering step of HIPE foam processing will generally be carried out until the HIPE foam is ready for use and is as dry as practical. Frequently such compression dewatered foams will have a water (moisture) content of from about 50 to about 500%, more preferably from about 50 to about 200%, by weight on a dry weight basis. Subsequently, the compressed foams can be thermally dried (e.g., by heating) to a moisture content of from about 5 to about 40%, more preferably from about 5 to about 15%, on a dry weight basis. The resulting compressed/dried foam will be in a collapsed, unexpanded state.

EXAMPLES

Preparation of collapsed HIPE absorbent foams of the type presently preferred for use in absorbent members of the present invention, and the characteristics of such collapsed foams, are illustrated by the following Examples, of which Example II A is the presently preferred material.

EXAMPLE I

This example illustrates the preparation of a collapsed HIPE foam falling within the scope of the present invention.

Emulsion Preparation

Anhydrous calcium chloride (36.32 kg) and potassium persulfate (568 g) are dissolved in 378 liters of water. This provides the water phase stream to be used in a continuous process for forming a HIPE emulsion.

To a monomer combination comprising styrene (1600 g), divinylbenzene 55% technical grade (1600 g), and 2-ethylhexylacrylate (4800 g) is added sorbitan laurate (960 g as SPAN ® 20). After mixing, this combination of materials is allowed to settle overnight. The supernatant is withdrawn and used as the oil phase in a continuous process for forming a HIPE emulsion. (About 75 g of a sticky residue is discarded.)

At an aqueous phase temperature of 48°-50° C. and an oil phase temperature of 22° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft holds 4 rows of pins, 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14 inches (35.6 cm) long with a 0.5 inch (1.3 cm) outside diameter. The static mixer is a TAH Industries Model 070–821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 1.127 g/sec oil phase and 2.19 cm$^3$/sec water phase.

Once the apparatus set-up is filled, agitation is begun in the dynamic mixer, with the impeller turning at 1800 RPM. The flow rate of the water phase is then steadily increased to a rate of 35.56 cm$^3$/sec over a time period of 130 sec. The back pressure created by the dynamic and static mixers at this point is 7.5 PSI (51.75 kPa). The impeller speed is then steadily decreased to a speed of 1200 RPM over a period of 60 sec. The back pressure drops to 4.5 PSI (31.05 kPa). At this point, the impeller speed is instantly increased to 1800 RPM. The system back pressure remains constant thereafter at 4.5 PSI (31.05 kPa).

Polymerization of the Emulsion

The formed emulsion flowing from the static mixer at this point is collected in Rubbermaid Economy Cold Food Storage Boxes, Model 3500. These boxes are constructed of food grade polyethylene and have nominal dimensions of 18"×26"×9" (45.7 cm×66 cm 22.9 cm). The true inside dimensions of these boxes are 15"×23"×9" (38.1 cm×58.4 cm×22.9 cm). These boxes are pretreated with a film of a solution comprising a 20% solution of SPAN ® 20 in an equal weight solvent mixture of xylene and 2-propanol. The solvent mixture is allowed to evaporate to leave only the SPAN ® 20. Forty-seven liters of emulsion are collected in each box.

The emulsion-containing boxes are kept in a room maintained at 65° C. for 18 hours to bring about polymerization of the emulsion in the boxes to thereby form polymeric foam.

Foam Washing and Dewatering

After curing is complete, the wet cured foam is removed from the curing boxes. The foam at this point contains about 30–40 times the weight of polymerized material (30–40×) of the residual water phase containing dissolved emulsifiers, electrolyte and initiator. The foam is sliced with a sharp reciprocating saw blade into sheets which are 0.350 inches (0.89 cm) in caliper. These sheets are then subjected to compression in a series of 3 nip rolls which gradually reduce the residual water phase content of the foam to about 6 times (6×) the weight of the polymerized material. At this point, the sheets are then resaturated with a 1% CaCl$_2$ solution at 60° C., are squeezed in a nip to a water phase content of about 10×, resaturated with the 1% CaCl$_2$ solution at 60° C., and then squeezed again in a nip to a water phase content of about 10×.

The foam sheets, which now contain about 10× of what is essentially a 1% CaCl$_2$ solution are passed through a final nip equipped with a vacuum slot. The last nip reduces the CaCl$_2$ solution content to about 5 times (5×) the weight of polymer. The foam remains compressed after the final nip at a caliper of about 0.080 in. (0.2 cm). The foam is then dried in an air circulating oven set at about 60° C. for about three hours. Such drying reduces the moisture content to about 5–7% by weight of polymerized material. At this point, the foam sheets have a caliper of about 0.075 in. (0.19 cm) and are very drapeable. The foam also contains about 11% by weight of residual sorbitan laurate emulsifier and about 5% by weight (anhydrous basis) of residual hydrated calcium chloride. In the collapsed state, the density of the foam is about 0.17 g/cm$^3$. When expanded in Jayco synthetic urine, its free absorbent capacity is about 30.2 mL/g. The expanded foam has a capillary suction specific surface area of about 2.24 m²/g, a pore volume of about 31 mL/g, a number average cell size of about 15 microns, an adhesion tension of about 35 dynes/cm, and a vertical wicking absorbent capacity of about 26.7 mL/g or about 88% of its free absorbent capacity.

EXAMPLE II

The following Examples illustrate the preparation of HIPE foams using sorbitan laurate (SPAN® 20) and polyglycerol fatty acid ester (PGE) or sorbitan palmitate (SPAN® 40) co-emulsifier systems:

EXAMPLE II A

Anhydrous calcium chloride (36.32 kg) and potassium persulfate (568 g) are dissolved in 378 liters of water. This provides the water phase stream used in forming the HIPE emulsion.

To a monomer mixture comprising styrene (1600 g), divinylbenzene (55% technical grade, 1600 g), and 2-ethylhexylacrylate (4800 g) is added sorbitan laurate (960 g as SPAN® 20). To another half-size batch of the same monomer mixture is added PGE emulsifier (480 g) that imparts a minimum oil/water IFT of 0.09 dynes/cm. This PGE is obtained by esterifying polyglycerols with fatty acids in a weight ratio of 64:36 using sodium hydroxide as the catalyst at 210° C. under conditions of mechanical agitation, nitrogen sparging and gradually increasing vacuum, with subsequent phosphoric acid neutralization, cooling to about 60° C., and settling to reduce unreacted polyglycerol. The composition of the polyglycerols and fatty acids used in making the PGE are shown in the following table:

|  | Wt. % |
|---|---|
| Polyglycerols | |
| linear diglycerols | 63.5 |
| triglycerol or higher | 36.0 |
| cyclic diglycerols | 0.4 |
| Fatty Acids | |
| C8 | — |
| C10 | — |
| C12 | 31.7 |
| C14 | 37.2 |
| C16 | 11.5 |
| C18:0 | 3.2 |
| C18:1 | 13.8 |
| C18:2 | 1.5 |

After mixing, each oil phase batch is allowed to settle overnight. The supernatant is withdrawn from each batch and mixed at a ratio of 2 parts of the SPAN® 20 containing oil phase to 1 part of the PGE containing oil phase. (About 75 g of a sticky residue is discarded from each of the batches.)

At an aqueous phase temperature of 43° to 45° C. and an oil phase temperature of 22° C., separate streams of the oil and water phases are fed to a dynamic mixer in the form of a pin impeller. This pin impeller has a cylindrical shaft of about 21.6 cm in length with a diameter of about 1.9 cm. The shaft holds 4 rows of pins, two rows having 17 pins and two rows having 16 pins, each pin having a diameter of 0.5 cm and extending outwardly 1.6 cm from the central axis of the shaft. The pin impeller is mounted within a cylindrical sleeve with the pins having a clearance of 0.8 mm from the inner wall.

A spiral static mixer (14 in. long by ½ in. outside diameter, TAH Industries Model 070-821, modified by cutting off 2.4 inches) is mounted downstream from the dynamic mixer to provide back pressure in the dynamic mixer and to provide uniformity in the HIPE emulsion. The combined dynamic and static mixer apparatus is filled with oil and water phases at a ratio of 2 parts water to 1 part oil. The apparatus is vented to allow air to escape until filling of the apparatus is complete. The flow rates during filling are 3.0 g/sec oil phase and 4.5 cc/sec water phase.

Once the apparatus is filled, agitation is begun, with the impeller turning at 1100 RPM. The aqueous phase flow rate is then evenly ramped up to 46.5 cc/sec and the oil phase flow rate is evenly ramped down to 1.77 g/sec over a time period of 120 sec. The back pressure created by the dynamic and static mixers at this point is 4.9 psi. Over a time period of 30 sec, the impeller is slowed to 1000 RPM. When the back pressure drops to approximately 3 psi, the impeller speed is then instantly increased to 1800 RPM, and the back pressure increased to 5.5 psi. The water and oil flows are then adjusted to 47.8 cc/sec and 1.66 g/sec, respectively.

The HIPE emulsion is collected in molds (round tubs with a central core). The molds are pretreated with a film of a solution comprising 20% SPAN® 20 in xylene which had been allowed to settle overnight to remove insolubles. The molds are preheated to facilitate the evaporation of the xylene and leave behind only the SPAN® 20. The filled molds are kept in a room maintained at 65° C. for 18 hours to allow for curing. After the foams are cured, they are cut to the desired thickness, as in Example I. The cured foam webs are then washed with a 1% calcium chloride solution. The residual solution retained in the foam before drying is 5 times the weight of foam.

Figure 3:
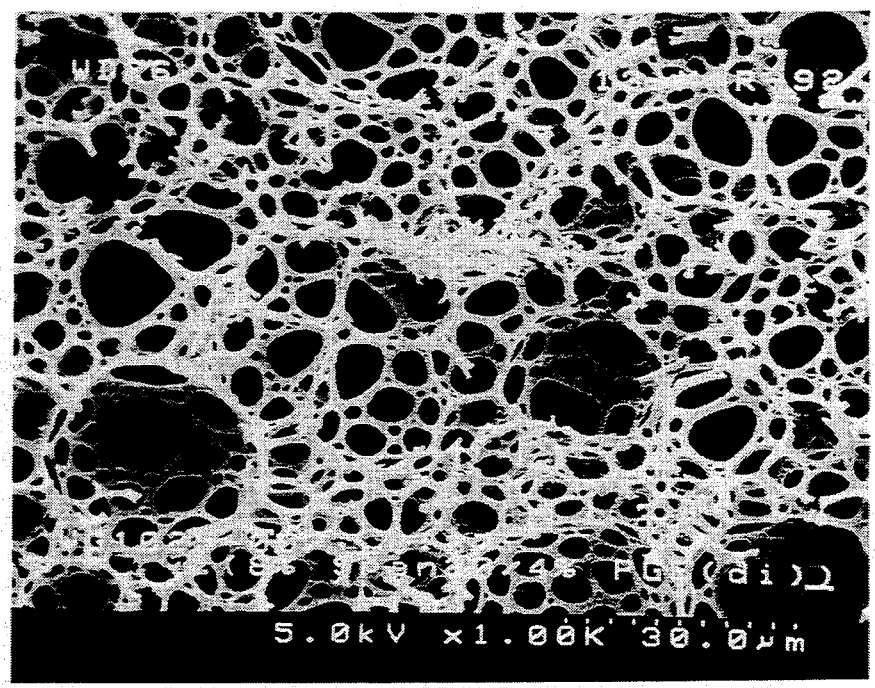
FIG. 3 of the drawings is a photomicrograph (1000× magnification) of a cut section of an absorbent polymeric foam according to the present invention that is prepared from a HIPE emulsion containing a preferred co-emulsifier system.

FIG. 3 is a photomicrograph (1000× magnification) that shows a representative polymeric foam prepared from a HIPE emulsion using a SPAN® 20/PGE co-emulsifier system like that of this example. The foam structure shown in FIG. 3 is in its expanded state. As can be seen, this foam structure has relatively small pores of relatively uniform size, i.e. the foam structure is relatively homogeneous. This suggests evidence of reduced coalescence of the water droplets during curing of the HIPE emulsion.

EXAMPLE II B

A water phase containing calcium chloride/potassium persulfate and an oil phase monomer mixture containing SPAN® 20 are prepared as in Example II A. To the monomer mixture is added sorbitan laurate (480 g as SPAN® 20) and a mixture of sorbitan laurate (240 g) and sorbitan palmitate (240 g as SPAN® 40). After mixing, the oil phase is allowed to settle overnight, with the supernatant being withdrawn for use in forming the HIPE emulsion.

The aqueous (48°–50° C.) and oil phases are then fed to the combined dynamic and static mixer apparatus as in Example II A. The combined apparatus is filled with the oil and water phases at a ratio of 2 parts water to 1 part oil, while venting the apparatus to allow air to escape until filling of the apparatus is complete. The flow rates during filling are 3.0 g/sec oil phase and 6 cc/sec water phase.

Once the apparatus is filled, agitation is begun, with the impeller turning at 1800 RPM. The aqueous phase flow rate is then evenly ramped up to 42.3 cc/sec and the oil phase flow rate is evenly ramped down to 1.5 g/sec over a time period of 60 sec. The back pressure is 4.5 psi. The HIPE emulsion is collected in molds (round tubs with a central core) and then kept in a room maintained at 65° C. for 18 hours to allow for curing, as in Example II A. After the foams are cured, they are cut to the desired thickness, as in Example I. The cured foam webs are washed with a 1% calcium chloride solution. The residual solution retained in the foam before drying is 5 times the weight of foam.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent member having a peripheral region and a deposition region contiguous with said peripheral region and laterally surrounded by said peripheral region, the absorbent member comprising:
   (a) at least one layer of absorbent material which, upon contact with aqueous body fluids, expands and absorbs said aqueous body fluids, said absorbent material comprising a hydrophilic, flexible structure of interconnected open spaces, said layer having an upper surface and a lower surface, said upper surface and said lower surface defining a planar direction and a normal direction perpendicular to said planar direction, said absorbent material being expandable in at least one direction within said planar direction in response to absorption of said aqueous body fluid into said interconnected open spaces; and
   (b) at least one slitted region comprising at least one slit extending at least partially through said layer, said slit comprising at least two slit surfaces which are displaceable with respect to one another when said aqueous body fluid is introduced into said deposition region and absorbed into said interconnected open spaces such that said slit opens and exposes said slit surfaces, the displacement of said slit surfaces being substantially reversible when said aqueous body fluid is removed from said interconnected open spaces and said absorbent material returns to an unexpanded state.

2. An absorbent member having a peripheral region and a deposition region contiguous with said peripheral region and laterally surrounded by said peripheral region, the absorbent member comprising:
   (a) at least one layer of absorbent material which, upon contact with aqueous body fluids, expands and absorbs said aqueous body fluids, said absorbent material comprising a collapsed polymeric foam material, said polymeric foam material comprising a hydrophilic, flexible structure of interconnected open cells, said layer having an upper surface and a lower surface, said upper surface and said lower surface defining a planar direction and a normal direction perpendicular to said planar direction, said absorbent material being expandable in at least one direction within said planar direction, said polymeric foam material having:
      (i) a specific surface area per foam volume of at least about 0.025 m²/cc;
      (ii) at least about 0.1% by weight of a toxicologically acceptable hygroscopic, hydrated salt incorporated therein;
      (iii) in its collapsed state, an expansion pressure of about 30 kPa or less; and
      (iv) in its expanded state, a density when saturated at 88° F. (31.1° C.) to its free absorbent capacity with synthetic urine having a surface tension of 65±5 dynes/cm of from about 10% to about 50% of its dry basis density in its collapsed state; and
   (b) at least one slitted region comprising at least one slit extending at least partially through said layer, said slit comprising at least two slit surfaces which are displaceable with respect to one another when said aqueous body fluid is introduced into said deposition region;
   whereby when said aqueous body fluid is introduced into said deposition region, at least a portion of said slitted region expands more rapidly than and to a greater degree than surrounding regions of said layer, and whereby at least a portion of said slitted region becomes deformed and buckled in said normal direction, thus causing said slit to open and expose said slit surfaces to said aqueous body fluid for more rapid acquisition.

3. The absorbent member of claim 2, wherein said polymeric foam material has a specific surface area per foam volume of at least about 0.05 m²/cc and a residual water content of at least about 4% by weight in its collapsed state.

4. The absorbent member of claim 3, wherein said polymeric foam material has:
   (a) a capillary suction specific surface area of from about 0.7 to about 8 m²/g;
   (b) from about 0.1 to about 8% by weight of calcium chloride, and from about 0.5 to about 20% by weight of a nonionic oil-soluble emulsifier incorporated therein to render the surface of the foam structure hydrophilic;
   (c) in its collapsed state:
      (i) a residual water content of from about 4 to about 30% by weight;
      (ii) a dry basis density of from about 0.05 to about 0.4 g/cm³;
   (d) in its expanded state:
      (i) a pore volume of from about 12 to about 100 mL/g;
      (ii) a resistance to compression deflection of from about 2 to about 80% when saturated at 88° F. (31.1° C.) to its free absorbent capacity with synthetic urine having a surface tension of 65±5 dynes/cm;
      (iii) a number average cell size of from about 5 to about 50 microns.

5. The absorbent member of claim 4, wherein said polymeric foam material has:
   (a) a capillary suction specific surface area of from about 1.5 to about 6 m²/g;
   (b) from about 3 to about 6% by weight of calcium chloride and from about 5 to about 12% by weight sorbitan laurate incorporated therein;
   (c) in its collapsed state:
      (i) a residual water content of from about 5 to about 15% by weight;
      (ii) a dry basis density of from about 0.1 to about 0.2 g/cm³;
      (iii) an expansion pressure of from about 7 to about 20 kPa;
   (d) in its expanded state:

(i) a pore volume of from about 25 to about 50 mL/g;
(ii) a resistance to compression deflection of from about 5 to about 40%;
(iii) a number average cell size of from about 5 to about 35 microns;
(iv) a density when saturated with said synthetic urine of from about 10 to about 30% of its dry basis density in its collapsed state.

6. An absorbent member having a peripheral region and a deposition region contiguous with said peripheral region and laterally surrounded by said peripheral region, the absorbent member comprising:
(a) at least one layer of absorbent material which, upon contact with aqueous body fluids, expands and absorbs said aqueous body fluids, said absorbent material comprising a hydrophilic, flexible structure of interconnected open spaces, said layer having an upper surface and a lower surface, said upper surface and said lower surface defining a planar direction and a normal direction perpendicular to said planar direction, said absorbent material being expandable in at least one direction within said planar direction in response to absorption of said aqueous body fluid into said interconnected open spaces; and
(b) at least one slitted region comprising at least one slit extending at least partially through said layer, said slit comprising at least two slit surfaces which are displaceable with respect to one another when said aqueous body fluid is introduced into said deposition region and absorbed into said interconnected open spaces, said slit surfaces having an initial orientation prior to introduction of said aqueous body fluid wherein said slit surfaces are substantially non-parallel and form an open receiving channel for enhanced acquisition of said aqueous body fluid into said interconnected open spaces.

7. The absorbent member of claim 6, wherein said absorbent material comprises a collapsed polymeric foam material, said polymeric foam material comprising a hydrophilic, flexible structure of interconnected open cells.

8. The absorbent member of claim 7, wherein said polymeric foam material has an expansion potential in at least one direction within said planar direction of at least 5%.

9. The absorbent member of claim 7, wherein said polymeric foam material has an expansion potential in at least two mutually orthogonal directions within said planar direction of at least 3%.

10. An absorbent member having a peripheral region and a deposition region contiguous with said peripheral region and laterally surrounded by said peripheral region, the absorbent member comprising:
(a) least one layer of absorbent material which, upon contact with aqueous fluids expands and absorbs said aqueous body fluids, said absorbent material comprising a hydrophilic, flexible structure of interconnected open spaces, said layer having an upper surface and a lower surface, said upper surface and said lower surface defining a planar direction and a normal direction perpendicular to said planar direction, said absorbent material being expandable in at least one direction within said planar direction in response to absorption of said aqueous body fluid into said interconnected open spaces; and
(b) at least one slitted region comprising at least one slit extending at least partially through said layer, said slit comprising at least two slit surfaces which are displaceable with respect to one another when said aqueous body fluid is introduced into said deposition region and absorbed into said interconnected open spaces such that said slit opens and exposes said slit surfaces to said aqueous body fluid for enhanced acquisition of said aqueous body fluid into said interconnected open spaces.

11. The absorbent member of claim 10, wherein said slit surfaces are displaceable with respect to one another in said normal direction.

12. The absorbent member of claim 10, wherein said slit surfaces are angularly displaceable with respect to one another.

13. The absorbent member of claim 10, further comprising an unslitted region at least partially surrounding said slitted region and extending outwardly from said slitted region.

14. The absorbent member of claim 1, wherein said absorbent member includes at least two layers of said absorbent material, and wherein said slitted region comprises at least one slit extending at least partially through at least one of said layers.

15. The absorbent member of claim 14, wherein said absorbent member comprises at least one layer provided with at least one slitted region and at least one layer which remains unslitted.

16. The absorbent member of claim 14, wherein said absorbent member includes at least one layer of hydrophilic fibrous material.

17. The absorbent member of claim 10, wherein said absorbent material comprises a collapsed polymeric foam material, said polymeric foam material comprising a hydrophilic, flexible structure of interconnected open cells.

18. The absorbent member of claim 17, wherein said polymeric foam material has an expansion potential in at least one direction within said planar direction of at least 5%.

19. The absorbent member of claim 17, wherein said polymeric foam material has an expansion potential in at least two mutually orthogonal directions within said planar direction of at least 3%.

20. The absorbent member of claim 17, wherein said polymeric foam material has an expansion potential in a direction parallel to the direction of said slit.

21. The absorbent member of claim 17, wherein said polymeric foam material has an expansion potential in a direction perpendicular to the direction of said slit.

22. The absorbent member of claim 17, wherein said polymeric foam material has an expansion potential both parallel and perpendicular to the direction of said slit.

* * * * *

UNITED STATES PATENT AND TRADEMARK OFFICE
CERTIFICATE OF CORRECTION

PATENT NO. : 5,397,316
DATED : March 14, 1995
INVENTOR(S) : GARY D. LAVON, ET AL.

It is certified that error appears in the above-identified patent and that said Letters Patent is hereby corrected as shown below:

In Column 18, line 60 of the patent, ".gaps" should read --gaps--.

In Column 27, line 31 of the patent, "palmirate" should read --palmitate--.

In Column 33, line 6 of the patent, "Mcintyre" should read --McIntyre--.

In Column 42, line 24 of the patent, "surrounding" should read --laterally surrounding--.

Signed and Sealed this

Eighth Day of October, 1996

Attest:

BRUCE LEHMAN

*Attesting Officer*  *Commissioner of Patents and Trademarks*